(12) United States Patent
Greenwald et al.

(10) Patent No.: US 7,526,389 B2
(45) Date of Patent: Apr. 28, 2009

(54) POWER MANAGEMENT OF A SYSTEM FOR MEASURING THE ACCELERATION OF A BODY PART

(75) Inventors: Richard M. Greenwald, Norwich, VT (US); Jeffrey J. Chu, Quechee, VT (US)

(73) Assignee: Riddell, Inc., Rosemont, IL (US)

( * ) Notice: Subject to any disclaimer, the term of this patent is extended or adjusted under 35 U.S.C. 154(b) by 314 days.

(21) Appl. No.: 11/031,970

(22) Filed: Jan. 6, 2005

(65) Prior Publication Data

US 2005/0177929 A1    Aug. 18, 2005

Related U.S. Application Data

(63) Continuation-in-part of application No. 10/997,832, filed on Nov. 24, 2004, which is a continuation of application No. 09/974,566, filed on Oct. 10, 2001, now Pat. No. 6,826,509, application No. 11/031,970.

(60) Provisional application No. 60/239,379, filed on Oct. 11, 2000, provisional application No. 60/609,555, filed on Sep. 13, 2004.

(51) Int. Cl.
  *G01F 17/00*    (2006.01)
  *A63B 71/10*    (2006.01)

(52) U.S. Cl. ............................................ 702/55; 2/425

(58) Field of Classification Search .................. 702/55, 702/141, 131, 138, 139; 2/422, 205, 421, 2/425; 73/514.01, 480; 340/669, 870.24, 340/870.01; 600/595

See application file for complete search history.

(56) References Cited

U.S. PATENT DOCUMENTS 3,972,038 A    7/1976    Fletcher et al.

(Continued)

FOREIGN PATENT DOCUMENTS

EP    0 315 498    5/1989

(Continued)

OTHER PUBLICATIONS

Reid, Stephen E, M.D, et al., "Head Protection in Football," *Sports Medicine*, Mar./Apr. 1974, pp. 86-92.

(Continued)

*Primary Examiner*—Michael P. Nghiem
*Assistant Examiner*—Toan M Le
(74) *Attorney, Agent, or Firm*—McDermott Will & Emery LLP

(57) ABSTRACT

The present invention provides an apparatus and method for determining the magnitude of linear and rotational acceleration of an impact to a body part. The apparatus can be used with protective sports equipment, such as a sports helmet, wherein the apparatus includes a battery, a number of accelerometers positioned proximate to the outer surface of the head, and an electronic device with a processor and a transmitter to transmit data received from the accelerometers. To maximize the battery life and minimize power consumption by the electronic device, the apparatus includes a power management system with a sensor assembly. The sensor assembly sends a first signal to the electronic device to initiate operation when the sensor assembly detects the presence of an object with the helmet, and a second signal to the electronic device to cease operation when the sensor assembly detects the absence of the object.

41 Claims, 9 Drawing Sheets

U.S. PATENT DOCUMENTS

| | | | |
|---|---|---|---|
| 4,196,429 A | 4/1980 | David | |
| 4,468,656 A | 8/1984 | Clifford et al. | |
| 4,590,801 A | 5/1986 | Merhav | |
| 4,665,748 A | 5/1987 | Peters | |
| 4,691,556 A | 9/1987 | Mellander et al. | |
| 4,873,867 A | 10/1989 | McPherson et al. | |
| 4,982,452 A * | 1/1991 | Chaise | 2/421 |
| 4,996,877 A | 3/1991 | Stewart et al. | |
| 5,383,363 A | 1/1995 | Kulmaczewski | |
| 5,487,305 A | 1/1996 | Ristic et al. | |
| 5,539,935 A | 7/1996 | Rush, III | |
| 5,546,609 A | 8/1996 | Rush, III | |
| 5,596,491 A * | 1/1997 | Gold | 363/65 |
| 5,615,132 A | 3/1997 | Horton et al. | |
| 5,621,922 A | 4/1997 | Rush, III | |
| 5,645,077 A * | 7/1997 | Foxlin | 600/587 |
| 5,697,099 A * | 12/1997 | Siska et al. | 2/5 |
| 5,704,707 A | 1/1998 | Gebelein et al. | 362/106 |
| 5,723,786 A | 3/1998 | Klapman | |
| 5,745,028 A | 4/1998 | Hock | |
| 5,819,206 A | 10/1998 | Horton et al. | |
| 5,856,811 A * | 1/1999 | Shih et al. | 345/8 |
| 5,896,590 A | 4/1999 | Fleisch | |
| 5,978,972 A * | 11/1999 | Stewart et al. | 2/422 |
| 6,009,563 A | 1/2000 | Swanson et al. | |
| 6,032,530 A | 3/2000 | Hock | |
| 6,298,483 B1 * | 10/2001 | Schiebl et al. | 2/9 |
| 6,301,718 B1 | 10/2001 | Rigal | |
| 6,361,507 B1 | 3/2002 | Foxlin | |
| 6,397,151 B1 | 5/2002 | Yamagishi et al. | |
| 6,406,168 B1 | 6/2002 | Whiting | 362/473 |
| 6,484,133 B1 | 11/2002 | Vogt | |
| 6,539,336 B1 | 3/2003 | Vock et al. | |
| 6,588,022 B1 * | 7/2003 | Anders et al. | 2/421 |
| 6,647,787 B2 | 11/2003 | Fore | |
| 6,730,047 B2 | 5/2004 | Socci et al. | |
| 2002/0116147 A1 | 8/2002 | Vock et al. | |
| 2002/0183657 A1 | 12/2002 | Socci et al. | |
| 2003/0014210 A1 | 1/2003 | Vock et al. | |
| 2003/0071766 A1 | 4/2003 | Harwell et al. | 345/8 |
| 2003/0163287 A1 | 8/2003 | Vock et al. | |
| 2003/0217582 A1 | 11/2003 | Reinbold et al. | |
| 2004/0008106 A1 | 1/2004 | Konczal | 340/432 |
| 2004/0240198 A1 | 12/2004 | Van Laar | 362/105 |
| 2006/0038694 A1 * | 2/2006 | Naunheim et al. | 340/665 |

FOREIGN PATENT DOCUMENTS

WO   WO 98/36213   8/1998

OTHER PUBLICATIONS

Padgaonkar, A.J. et al., "Measurement of Angular Acceleration of a Rigid Body Using Linear Accelerometers," *Journal of Applied Mechanics*, Sep. 1975, pp. 552-556.

Moon, Donald W., et al., "Peak Head Acceleration of Athletes During Competition—Football," *Medicine and Science in Sports*, Spring 1971, pp. 44-50, vol. 3 No. 1.

Medendorp et al., "Off-centric Rotation Axes in Natural Head Movements: Implications for Vestibular Reafference and Kinematic Redundancy," *The American Physiological Society*, 1998, pp. 2025-2039.

Foxlin et al., "Miniature 6-DOF Inertial System for Tracking HMDs," *SPIE, Helmet and Head-Mounted Displays III, AeroSense 98*, vol. 3362.

* cited by examiner

POWER MANAGEMENT OF A SYSTEM FOR MEASURING THE ACCELERATION OF A BODY PART

CROSS-REFERENCE TO RELATED APPLICATIONS

This application is a Continuation-in-Part of co-pending application Ser. No. 10/997,832 filed Nov. 24, 2004, which is a Continuation of application Ser. No. 09/974,566 filed Oct. 10, 2001, now U.S. Pat. No. 6,826,509 issued Nov. 30, 2004, which claims the benefit of Provisional Application No. 60/239,379 filed Oct. 11, 2000. Further, this application also claims priority to Provisional Application No. 60/609,555 filed Sep. 13, 2004.

FEDERALLY SPONSORED RESEARCH OR DEVELOPMENT

The invention described herein was made in the course of work under grant number 1R43HD4074301 from the National Institutes of Health. The U.S. Government may retain certain rights in this invention.

BACKGROUND OF THE INVENTION

The present invention relates to recording of the magnitude and direction of impact to and the linear and rotational acceleration of a body part, such as a human head, of person engaged in physical activity, such as during the play of a sport.

More particularly, it relates to a helmet based system which is typically worn while playing a sport such as football or hockey, and to the method of recording and storing data relating to the linear and rotational accelerations of the person's body part due to impact forces acting thereon. The present invention relates also to head mounted systems which are also worn during game play, such as a head band, that does not employ helmets, such as soccer.

It should be understood that the present invention relates generally to the linear and rotational acceleration of a body part, and most importantly, the head. The present invention, as will be discussed in detail below, is capable of monitoring any body part of an individual but has particular application in monitoring the human head. Therefore, any reference to a body part is understood to encompass the head and any reference to the head alone is intended to include applicability to any body part. For ease of discussion and illustration, discussion of the prior art and the present invention is directed to the head of human, by way of example and is not intended to limit the scope of discussion to the human head.

There is a concern in various contact sports, such as football and hockey, of brain injury due to impact to the head. During such physical activity, the head or other body part of the individual, is often subjected to direct contact to the head which results in impact to the skull and brain of the individual as well as movement of the head or body part itself.

Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality. Almost all of what is known is derived from animal studies, studies of cadavers under specific directional and predictable forces (i.e. a head-on collision test), from crash a dummies, from human volunteers in well-defined but limited impact exposures or from other simplistic mechanical models. The conventional application of known forces and/or measurement of forces applied to animals, cadavers, crash dummies, and human volunteers limit our knowledge of a relationship between forces applied to a living human head and resultant severe and catastrophic brain injury. These prior studies have limited value as they typically relate to research in the automobile safety area.

The concern for sports-related injuries, particularly to the head, is higher than ever. The Center for Disease Control and Prevention estimates that the incidence of sports-related mild traumatic brain injury (MTBI) approaches 300,000 annually in the United States. Approximately ⅓ of these injuries occur in football. MTBI is a major source of lost player time. Head injuries accounted for 13.3% of all football injuries to boys and 4.4% of all soccer injuries to both boys and girls in a large study of high school sports injuries. Approximately 62,800 MTBI cases occur annually among high school varsity athletes, with football accounting for about 63% of cases. Concussions in hockey affect 10% of the athletes and make up 12%-14% of all injuries.

For example, a typical range of 4-6 concussions per year in a football team of 90 players (7%), and 6 per year from a hockey team with 28 players (21%) is not uncommon. In rugby, concussion can affect as many as 40% of players on a team each year. Concussions, particularly when repeated multiple times, significantly threaten the long-term health of the athlete. The health care costs associated with MTBI in sports are estimated to be in the hundreds of millions annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Athletes who suffer head impacts during a practice or game situation often find it difficult to assess the severity of the blow. Physicians, trainers, and coaches utilize standard neurological examinations and cognitive questioning to determine the relative severity of the impact and its effect on the athlete. Return to play decisions can be strongly influenced by parents and coaches who want a star player back on the field. Subsequent impacts following an initial concussion (MTBI) may be 4-6 times more likely to result in a second, often more severe, brain injury. Significant advances in the diagnosis, categorization, and post-injury management of concussions have led to the development of the Standardized Assessment of Concussion (SAC), which includes guidelines for on-field assessment and return to sport criteria. Yet there are no objective biomechanical measures directly related to the impact used for diagnostic purposes. Critical clinical decisions are often made on the field immediately following the impact event, including whether an athlete can continue playing. Data from the actual event would provide additional objective data to augment psychometric measures currently used by the on-site medical practitioner.

Brain injury following impact occurs at the tissue and cellular level, and is both complex and not fully understood. Increased brain tissue strain, pressure waves, and pressure gradients within the skull have been linked with specific brain injury mechanisms. Linear and rotational head acceleration are input conditions during an impact. Both direct and inertial (i.e. whiplash) loading of the head result in linear and rotational head acceleration. Head acceleration induces strain patterns in brain tissue, which may cause injury. There is significant controversy regarding what biomechanical information is required to predict the likelihood and severity of MTBI. Direct measurement of brain dynamics during impact is extremely difficult in humans.

Head acceleration, on the other hand, can be more readily measured; its relationship to severe brain injury has been postulated and tested for more than 50 years. Both linear and rotational acceleration of the head play an important role in producing diffuse injuries to the brain. The relative contributions of these accelerations to specific injury mechanisms have not been conclusively established. The numerous mechanisms theorized to result in brain injury have been evaluated in cadaveric and animal models, surrogate models, and computer models. Prospective clinical studies combining head impact biomechanics and clinical outcomes have been strongly urged. Validation of the various hypotheses and models linking tissue and cellular level parameters with MTBI in sports requires field data that directly correlates specific kinematic inputs with post-impact trauma in humans.

In the prior art, conventional devices have employed testing approaches which do not relate to devices which can be worn by living human beings, such as the use of dummies. When studying impact with dummies, they are typically secured to sleds with a known acceleration and impact velocity. The dummy head then impacts with a target, and the accelerations experienced by the head are recorded. Impact studies using cadavers are performed for determining the impact forces and pressures which cause skull fractures and catastrophic brain injury.

There is a critical lack of information about what motions and impact forces lead to MTBI in sports. Previous research on football helmet impacts in actual game situations yielded helmet impact magnitudes as high as 530 g's for a duration of 60 msec and >1000 g's for unknown durations with no known MTBI. Accelerometers were held firmly to the head via the suspension mechanism in the helmet and with Velcro straps. A recent study found maximum helmet accelerations of 120 g's and 150 g's in a football player and hockey player, respectively. The disparity in maximum values among these limited data sets demonstrates the need for additional large-scale data collection.

Most prior art attempts relate to testing in a lab environment. However, the playing field is a more appropriate testing environment for accumulating data regarding impact to the head. A limitation of the prior art involves practical application and widespread use of measurement technologies that are size and cost effective for individuals and teams. Therefore, there would be significant advantage to outfitting an entire playing team with a recording system to monitoring impact activities. This would assist in accumulating data of all impacts to the head, independent of severity level, to study the overall profile of head impacts for a given sport. Also, full-time head acceleration monitoring would also be of great assistance in understanding a particular impact or sequence of impacts to a player's head over time that may have caused an injury and to better treat that injury medically.

To address this need, there have been many attempts in the prior art to provide a system for recording the acceleration of an individual's body part, such as their head. For example, prior art systems have employed tri-axial accelerometers which are affixed as a module to the back of a football helmet. Such tri-axial accelerometers provide acceleration sensing in the X, Y and Z directions which are orthogonal to each other. Tri-axial accelerometer systems require that the accelerometers be orthogonal to each other Also, such tri-axial accelerometer systems have been extremely expensive making it cost prohibitive for widespread commercial installation on an entire team.

Prior art systems, have also attempted to precisely locate the various combinations of linear and rotational accelerometers, in specific orthogonal arrays, within a helmet to obtain complete three-dimensional head kinematics. Such arrays require that the accelerometers be positioned orthogonal to each other. It is impractical, from a size, cost and complexity standpoint, for commercial application of such arrays in helmet or head mounted systems.

Obviously, accelerometer arrays for measuring linear and rotational accelerations cannot be readily mounted inside the human head, as is done with instrumented test dummy heads. Other sensing technologies, such as gyroscopes, magnetohydrodynamic angular rate sensors and GPS sensors, do not currently fulfill the practical and technical specifications for a commercially available system. Also, the use of multi-axis accelerometer systems placed in a mouthguard are impractical because wires need to run from the helmet or backpack into the user's mouth from the power source and to a telemetry unit, which might present a hazard to the players and limited compliance among them.

In view of the foregoing, there is a demand for a head acceleration sensing system that can be manufactured and installed at very low cost to permit widespread utilization. There is a demand for a system that can be installed in many, many individuals, such as an entire football team roster of over 60 players, to provide research opportunities and data that have not yet been available to the scientific community before. Further, there is a demand for a system and method for measuring the linear and rotational acceleration of a body part that is easy to install and comfortable for the individual to wear. There is also a desire to provide a low-cost system and method that can record and accurately estimate linear and rotational acceleration of a body part.

The present invention is provided to solve the problems discussed above and other problems, and to provide advantages and aspects not provided by prior designs of this type. A full discussion of the features and advantages of the present invention is deferred to the following detailed description, which proceeds with reference to the accompanying drawings.

SUMMARY OF THE INVENTION

The present invention preserves the advantages of prior art body part acceleration systems and associated methods. In addition, it provides new advantages not found in currently available methods and systems and overcomes many disadvantages of such currently available methods and systems.

The invention is generally directed to the novel and unique head acceleration monitoring technology that is a highly portable system that designed to measure and record acceleration data in linear directions and to estimate rotational accelerations of an individual's head and direction and magnitude of impact during normal activity, such as during game play. While the present invention is specifically developed for the head, monitoring of other body parts, or the body in general, is envisioned and considered within the scope of the present invention.

The system and method of the present invention offers the opportunity to study head acceleration, human tolerance limits, the range and direction of accelerations in humans in relation to morphological features (e.g., neck circumference, head volume, neck length), and the relationship between precise measures of head acceleration in linear and rotational directions and acute consequence to brain physiology and function. Moreover, it provides the ability to measure an individual's cumulative exposure to linear and rotational accelerations while allowing unaffected performance of everyday sports and activities.

The system and method of the present invention is designed as a standard component of otherwise conventional sporting gear, in particular the helmet or as an independent head mounted system. The system and method of the present invention is designed for determining the magnitude of linear acceleration and direction of impact to a body part as well as the rotational acceleration of a body part, such as a head. A number, such as three, single-axis accelerometers are positioned proximal to the outer surface of the body part and about a circumference of the body part in a known spaced apart relation from one another. The accelerometers are oriented to sense respective linear acceleration orthogonal to the outer circumference of the body part. Dual-axis, tri-axis, or rotational accelerometers may also be employed to provide an additional direction of acceleration sensing which is tangential to the surface of the skull of the head. Such tangential acceleration data may be optionally employed in further analysis.

The acceleration data sensed is recorded for each accelerometer. A hit profile function is determined from the configuration (i.e. geometry) of the body part and the positioning of the plurality of accelerometers thereabout. A number of potential hit results are generated from the hit profile function and then compared to the acceleration data sensed by the accelerometers. One of the potential hit results is best fit matched to the acceleration data to determine a best fit hit result. The magnitude acceleration and direction of acceleration due to an impact to the body part are determined from applying the hit profile function to the best fit hit result. The rotational acceleration of the body part can also be estimated from the magnitude and direction of the impact to the body part.

The data recorded is either recorded on a memory card or other mass memory means installed locally in the helmet, or is transmitted to a nearby receiver for storage on a computer's hard drive or other conventional mass storage device using conventional telemetry technology. The present invention provides storage of data over a length of time such that cumulative exposure effects and thus limits can be established for further or future participation in the sport by the individual wearing the helmet equipped with the present invention. The data also allows detection of impacts to the head which precede the occurrence of a brain injury. For this purpose the system and method of the present invention could be modified to record detailed data only when the accelerations exceed a defined threshold. The data may be processed immediately as the data is recorded, or at a later time so as to integrate and otherwise determine the linear, rotational and normal components of acceleration of the player's head.

The present invention is applicable for use with other parts of the body. For instance, other applications could include the study of the acceleration of body parts in relation to each other (e.g., among pole vaulters, high jumpers, or gymnasts), or to understand factors affecting acceleration in sprinters and swimmers (e.g., starting and turns).

Because of its portability, small size, and convenient light weight, the system and associated method of the present invention can also be used to study the acceleration of the body parts of live animals. For example, the acceleration and deceleration of birds in flight could be studied with a modified version of the present invention.

Therefore, the present invention employs accelerometers arranged in a manner orthogonal to the surface of the body part instead of arrays of accelerometers orthogonal to each other. The invention provides an inexpensive system that can still achieve results which are within the acceptable range of error for the given scientific question, study or hypothesis.

Another aspect of the present invention is to provide a system and method of calculating and estimating the linear and rotational acceleration that is easy to install and is comfortable for the individual to wear without affecting their game play either in a helmet or head band environment. It is yet another object of the present invention to provide a system and method of measuring and calculating the linear and rotational acceleration that can be installed commercially at low cost.

A further aspect of the invention is to provide a power management system for the battery powered electronic device(s) associated with protective sports equipment, including the helmet. The power management system includes a sensor assembly that sends a first signal to the electronic device to initiate operation when the sensor assembly detects the presence of an object. The sensor assembly sends a second signal to the electronic device to cease operation when the sensor assembly detects the absence of the object. The sensor assembly generates the first signal when the object is at a first distance from the sensor, and generates the second signal when the object is at a second distance from the sensor. The sensor assembly includes a proximity sensor, which may be an inductive sensor, a capacitive sensor, a photoelectric sensor, or an ultrasonic sensor.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
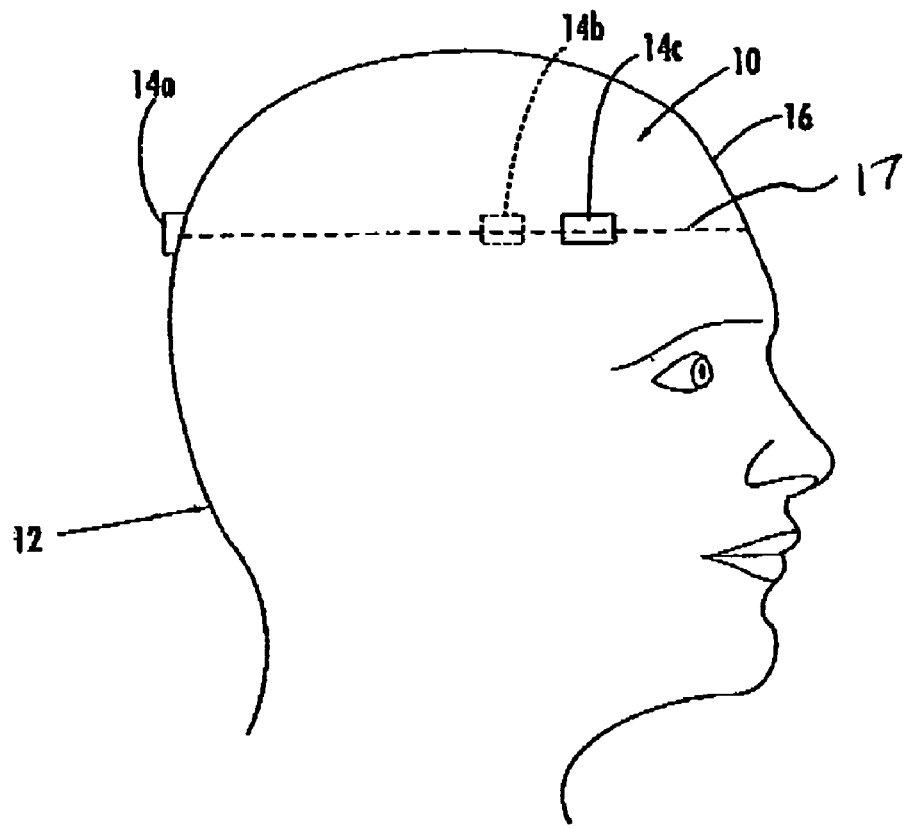
FIG. 1 is a side view the system of the present invention installed in a football helmet on an individual's head.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention provides a system and method for measuring, i.e. estimating, the linear and rotational acceleration of a body part. For ease of illustration, the body part will be described below as a human head, however,. Unlike the prior art, the present invention uses single axis accelerometers orthogonal to the surface of the body part and not necessarily orthogonal to each other to enable the estimation of both the linear acceleration and rotational acceleration of the body part.

Figure 2:
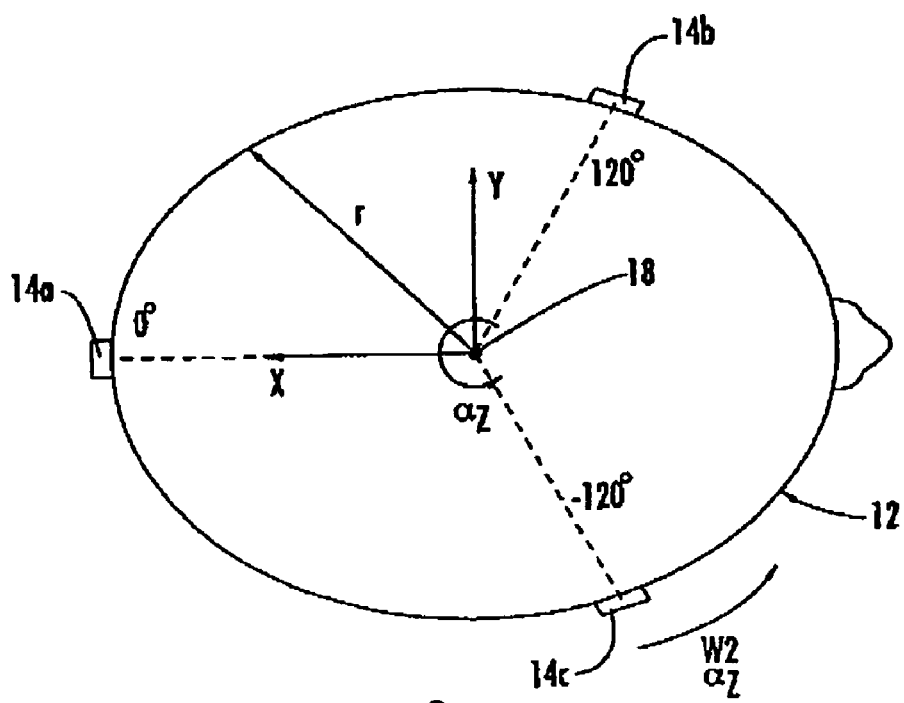
FIG. 2 is a top view of the system shown in FIG. 1.

Referring first to FIG. 1, a side view of an installed system 10 of the preferred embodiment of the present invention is shown installed on body part 12, namely a human head. FIG. 2 shows a top view of this system 10 of the preferred embodiment of the present invention. The system 10 includes an array of accelerometers, generally referenced as 14, positioned about the periphery of the skull 16 of the head 12. Preferably, an array of 3 accelerometers 14 or more are located as close as possible to the outer surface of the skull 16 and arranged in the same plane which preferably passes through the center of gravity 18 of the body part 12. However, less than three accelerometers 14 may be used and the arrangement of the accelerometers 14 may be in different configurations around the surface of the skull, provided that their sensitive axis is orthogonal to the surface of the skull. The array of accelerometers are arranged in a band configuration 17 (see FIG. 1) about the skull 16 of the head 12.

In the preferred embodiment shown in FIGS. 1 and 2, an array of three accelerometers 14a, 14b and 14c are provided and are positioned at known positions about the outer periphery of the skull 16. As shown in FIG. 2 and in accordance with the coordinate system defined in FIG. 3, accelerometer 14a is positioned at 0 degrees while accelerometer 14b is positioned at 120 degrees and accelerometer 14c at −120 degrees. The use of as few accelerometers 14 as possible to estimate linear and rotational acceleration of the head 12 within a prescribed error tolerance is balanced against the cost associated of the system, namely the added cost per accelerometer 14 and associated circuitry 15 employed. If greater accuracy of the estimation of the linear and rotational acceleration of the head 16 is desired, the number of accelerometers 14 may be increased to improve the overall "goodness of fit" of the actual acceleration measurements to the estimation of linear and rotational acceleration of the head 16.

Figure 4:
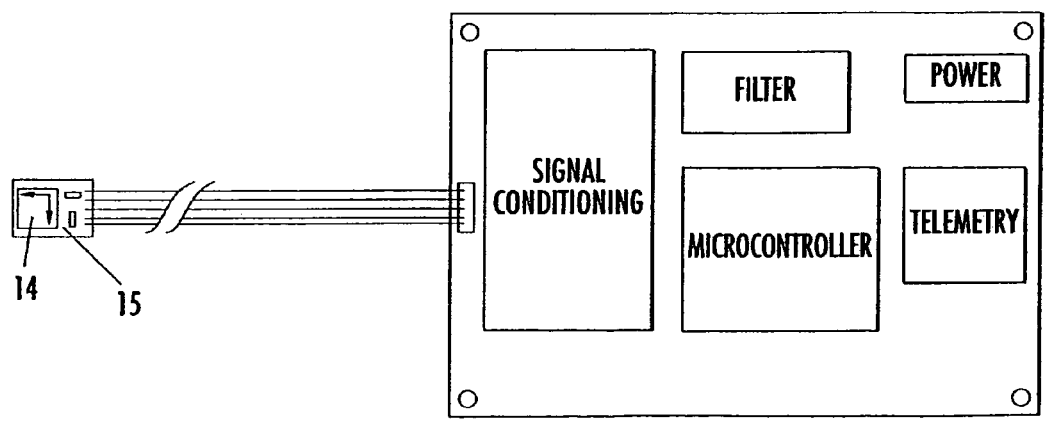
FIG. 4 is a perspective view of an accelerometer employed in the present invention.

The Analog Devices ADXL193/278 family of accelerometers are preferred for use in the system 10 of the present invention. An example of a preferred accelerometer 14 is shown in FIG. 4. The ADXL278 is similar to the ADXL 193 except that it is a two-axis accelerometer rather than single-axis. Critical specifications include: small size (4.5 mm×4.5 mm×2.0 mm), low mass (1.5 g), operation at 3.3 V, high output (250 g max), high sensitivity (27 mv/g) and low cost. One axis measures accelerations towards the center of the head, while the second axis measures acceleration tangential to the surface of the head. While a single-axis accelerometer 14 is preferred, the second axis measurement of the ADXL 278 can also provided additional acceleration information for further processing and analysis. This second axis includes additional data tangential to the head during rotational experiments in the laboratory. While the ADXL 193/278 family of accelerometers are preferred, other accelerometers 14 may be employed to carry out the present invention.

In accordance with the present invention, the accelerometers 14 must be held close to the skull 16 of the head 12 to best measure the acceleration of the head. Direct attachment of accelerometers to the head is optimal but not feasible. Attempts to mount accelerometers directly to the helmet shell result in measures of helmet deformation rather than head acceleration. Variations among football helmet padding and liners and other helmet designs for other sports demand generic mounting concepts that are universally applicable. Thus, the mounting of the accelerometers 14 should not alter helmet performance or protrude from existing internal padding more than 1 mm. Also, the accelerometers 14 should be contained within and/or attached to the helmet to allow easy removal of both the helmet or headband and the accelerometers 14.

Figure 5:
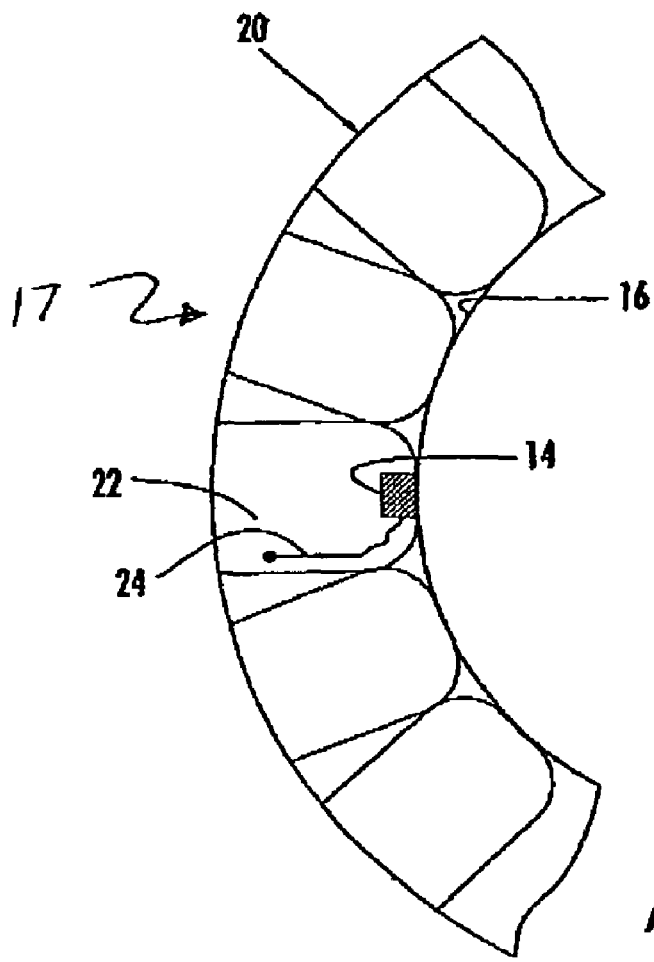
FIG. 5 is a side elevational view of a accelerometer embedded within cushioning of a football helmet.

The present invention provides a structure for maintaining the accelerometers 14 in a position as close as possible to the skull 16 while being as comfortable as possible. As shown in FIG. 5, it has been discovered that the preferred structure for positioning of the accelerometers proximate to the skull is to contain the accelerometers 14 within an air bladder 22 mounted within the helmet, generally referenced as 20.

As shown in FIG. 5, in one embodiment the accelerometers 14 are positioned inside an air-bladder 22 itself such that the pressure inside the bladder 22 will provide the force necessary to place the accelerometer 14 in direct apposition to the skull 16 of the head 12 when the bladder 22 is inflated. Additional accelerometers 14 are respectively placed in appropriately positioned air bladders 22 within the helmet 20 to provided the array of accelerometers as described above. In accordance with this attachment method, an RF welding process can be employed to pass the requisite cabling 24 through the bladder seal without compromising the integrity of the bladder 22. A significant advantage of this method is that, for a given padding configuration, the accelerometers 14 will be oriented similarly for all players using that model helmet 20.

Figure 6:
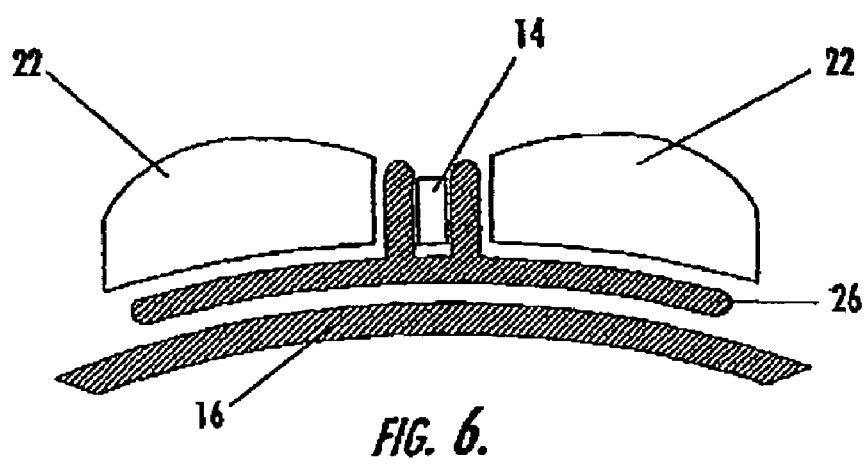
FIG. 6 is a side elevational view of an accelerometer held in place in a helmet by a T-shaped holder.

Alternatively, as shown in FIG. 6, the accelerometers 14 may be respectively installed in a plastic T-shaped holder 26 for placing the accelerometers 14 approximately in apposition to the skull 16 of the head 12. Each plastic T-shaped holder 26 respectively holds an accelerometer 14 between the cushions 22 in a football helmet and in direct apposition to the surface of the skull 16. This T-shaped accelerometer holder 26, for example, may be constructed of Delrin and with a 4 mm slot 28 for holding and orienting the accelerometer 14. The T-shaped holder 26 is pressed against the skull 16 of the head 12 when the air bladders 22 are inflated to 20 psi, for example. Depending upon packaging, this structure for positioning the accelerometers 14 may not be preferred because it is possible that the users could feel the accelerometers 14 pushing against the skull 16 of their head 12.

Also, direct attachment of the accelerometers 14 to the air bladder 22 of the helmet 20 with a foam covering (not shown) is possible, although not preferred, because the sensitive axis of these devices is along a plane parallel to the top of the device. The minimum dimension of the accelerometer 14 and its mounting board 15, as shown in FIG. 4, in that direction is 7 mm, which caused the unit to act effectively as a point source against the head 12.

Still further and within the scope of the present invention, a mesh net or bandana carrying the array of accelerometers 14 units may be worn on the head or coupled to the inside of the helmet or a multi-layer soft foam interface that captured the accelerometers between layers or a spring-loaded construct attached to the shell of the helmet 20 between the foam pads (not shown) and air bladders 22.

Figure 7:
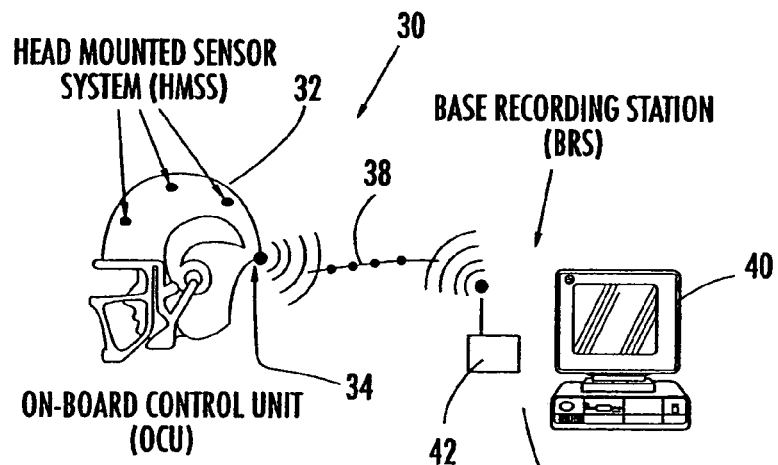
FIG. 7 is a diagram illustrating the wireless telemetry system optionally employed in the present invention.

As shown in FIG. 7, the above described array of accelerometers 14 are electrically interconnected together to form an entire system 30 for the collection, recording and processing of head acceleration data. The system 30 includes the accelerometers 14 which define a head-mounted sensor system (HMSS), generally referred to as 32, an on-board control unit (OCU), generally referred to as 34, and a base recording station (BRS), generally referred to as 36. Preferably, the data connection 38 between the OCU 34 and BRS 36 is wireless, however, a hardwired, tethered connection 38 is also possible.

Together, these components provide a telemetered data acquisition system 30 for monitoring and recording sensor data on head impacts. The installed environment for the HMSS 32 need not always be a helmet, and can be adapted for use in various forms in helmets or headgear for sports including football, hockey, soccer, lacrosse, wrestling, boxing and others. Further, the HMSS 32 can be configured for use with protective equipment for a body other than the head, such as a knee, chest, rib or shoulder pad. The HMSS unit 32 can be comprised of various additional sensors including displacement, load, pressure, acceleration, temperature, etc. In the current configuration, the HMSS 32 system is composed of multiple accelerometers 14 as described above.

In FIG. 7, the BRS 36 and OCU 34 are preferably specified to be active during all practice and game situations. For team or multiple user configurations, the BRS 36 is either a laptop or PC 40, which is serially linked to a receiver 42 with capability for simultaneous transmission from a large number of individuals, for example one hundred OCU transmitters 34. Calculations show that at a data transfer rate of 19.2 kbps, with maximum 100 bytes of information from each OCU 34 per impact, data from all 22 players on the field at any one time in sports such as soccer or football could be downloaded to the BRS 36 within 1 second. For single user configuration where a single OCU 34 transmits to a single BRS 36, the BRS 36 could be a stand-alone data-logger, or could be contained internally within the OCU 34, with plug in capability for downloading of data and programming. Triggering conditions programmed into the OCU 34 activate the telemetered data acquisition system 30, including the accelerometers 14, and send information to the BRS 36. Power is conserved by turning the transmitter portion of the OCU 34 on only when an impact event occurs. For example, a minimum acceleration of 10 g's might be set as the trigger. Each OCU 34 uniquely identifies a given helmet 20 in the field and encodes the information so that the BRS 36 can properly multiplex and decode information from multiple OCU's. For example, standard 128-bit encryption technology can be utilized to maintain the security of the transmitted data.

In accordance with the present invention, a miniature telemetry system 30 is provided with a transmitter/receiver or transreceiver that preferably operates in the industrial, scientific, and medical (ISM) radio bands range with a range of at least 150 meters. For example, the transmitter/receiver operates at 900 MHz, 2.4 GHz, or 5.8 GHz. Analog signals from the accelerometers 14 will be time-division multiplexed (TDM) for transmission to the BRS. The size of the OCU 34 is specified to be no larger than 5 cm long×2.5 cm high×2.5 cm wide, or the size of 2 small AA batteries. The OCU 34 can be mounted at the base of the helmet 20 in the rear just above the neckline without interfering with player motion and without creating an injury hazard. The OCU 34 must contain the battery, the transmitter, and signal conditioning for the accelerometers. Alternatively, the OCU 34 contains a processor, the transmitter, and signal conditioning for the accelerometers, wherein the battery is spaced a distance from the OCU 34 but remains operably connected thereto.

The preferred accelerometers 14 operate at 3.3 V, the amplifier boards 15 power the accelerometers 14 and provide signal conditioning for the raw accelerometer signals with a high pass filter, that ranges between 0.5 to 10 Hz, to eliminate static measurements (such as player shaking his head). The chips of the ADXL93/278 accelerometers have a 400 Hz 2-pole Bessel filter on-board. An additional 3000 Hz low pass, anti-aliasing filter on the amplifier board reduced high frequency noise that might enter the circuit after the accelerometer chip 15 and before the amplifier.

Details of the above system 30 set forth a preferred construction for carrying out the present invention. Such a system 30 may be modified to suit the needs of the particular application at hand, namely the environment of installation, required capacity, durability and cost. Such modified systems 30 are deemed to be within the scope of the present invention.

Acceleration data is collected and recording for each of the accelerometers 14 in the system 30 as described above. This data must be processed for meaningful analysis. Specifically, in accordance with the present invention, the actual linear and rotational acceleration of the head and the magnitude of the impact is estimated using the arrangement of single-axis accelerometers 14 in the system 30 as described above.

The data collected and recorded by the accelerometers is processed according to a novel algorithm of the present invention. The processing of the data with the novel algorithm of the present invention assumes that: 1) the accelerometers 14 are placed at known locations around the surface of the skull 16 of the head 12, as shown in FIG. 2; and 2) the surface of the skull 16 of the head 12 can be described geometrically.

Figure 3:
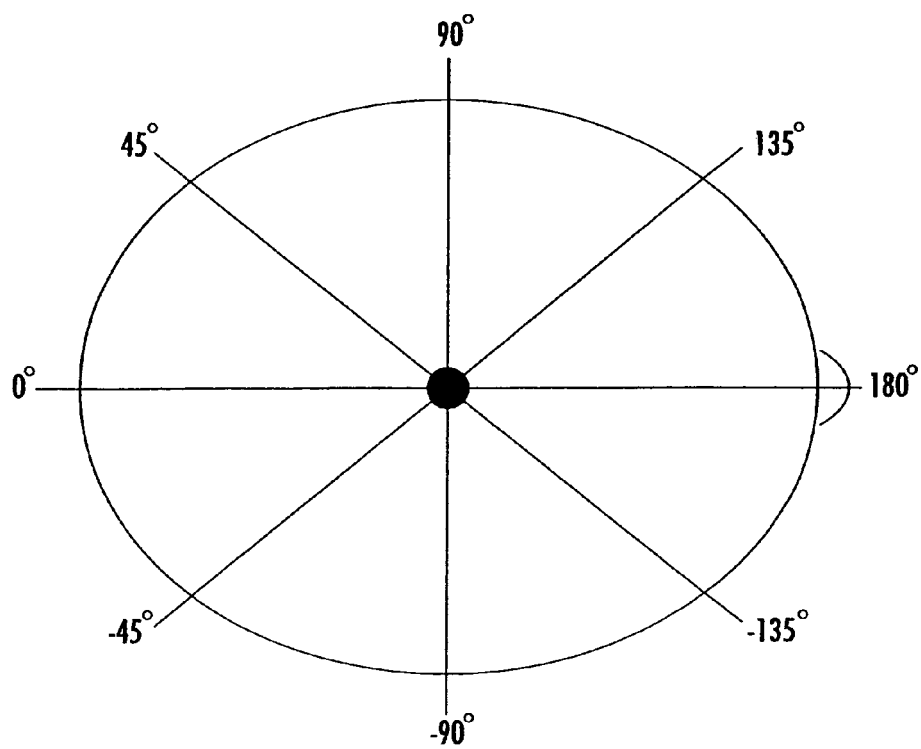
FIG. 3 is a schematic top view of a head with a coordinate system shown thereon.

For example, the novel algorithm can be demonstrated for a typical case where, in addition to the above assumptions, the following conditions are met: 1) the accelerometers 14 are placed at known locations around the transverse plane of the skull 16 of the head 12 passing through a point 18 located approximate to the center of gravity, as shown in FIG. 2; 2) the head cross-section (HCS) in this transverse plane is circular, and defines a radial coordinate system, as shown in FIG. 3; and 3) the impact is linear and lies within the transverse plane.

For these conditions, it can be shown that the magnitude of the linear acceleration normal to the HCS varies as the cosine of the arc (s) along the HCS. A Hit Profile is defined by the following function:

$$a*\cos(s-b)+c \quad (1)$$

where a=peak linear head acceleration (g's), s=arc (deg), b=hit location on the head (deg) and c=the offset. For a given impact and a specific configuration of accelerometers 14, i.e. the number and location of accelerometers 14, there will be a set of n acceleration profiles and peak accelerations. Given the location of each accelerometer, in degrees, in the HCS, a least-squares fit of the acceleration data to the Hit Profile yields the predicted peak linear head acceleration, a, and the predicted hit location, b, in the HCS. In the case where the impact is directed to the center of gravity of the head 12, the offset will be zero. Otherwise, as will be described below, axial rotational head acceleration will result requiring an offset value.

In general, the acceleration data is collected and recorded. A hit profile function is determined from the configuration of the body part and the positioning of the plurality of accelerometers thereabout. A number of potential hit results are generated from the hit profile function and then compared to the acceleration data sensed by the accelerometers. One of the potential hit results is best fit matched to the acceleration data to determine a best fit hit result. The magnitude and direction of an impact to the body part is determined from applying the hit profile function to the best fit hit result. The rotational acceleration of the body part can also be determined from the magnitude and direction of the impact to the body part and the offset.

EXAMPLE OF APPLICATION OF ALGORITHM

Figure 8:
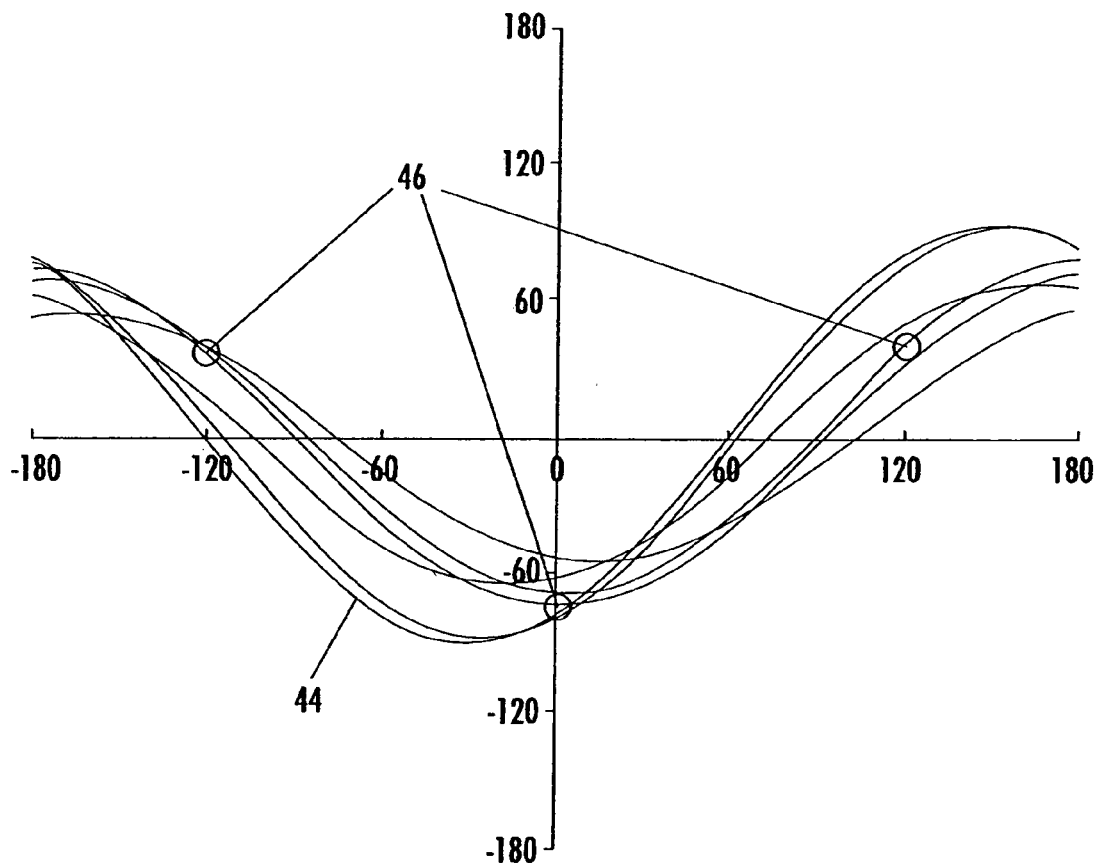
FIG. 8 is a graphical display of the fitting of the algorithm to the collected data.

As shown in FIG. 8, the acceleration data for a given array of three accelerometers is graphically displayed in two dimensions. In this example, the accelerometers are placed at the known locations of (−)120 degrees, 0 degrees and 120 degrees about the assumed circular circumference of the skull of a head with a known arc length s which is the radius r in FIG. 2. In this example, the accelerometers revealed an impact by sensing the following accelerations:

TABLE 1

| Location of Accelerometer in Coordinate System | Peak Acceleration Sensed (g) |
|---|---|
| (−)120 | 75 |
| 0 | 8 |
| 120 | 75 |

These known parameters of the location of the accelerometers are used to create series of cosine waves from the above algorithm function which are each slightly different than one another. This series of waveforms correspond to the various potential hit magnitudes and hit locations calculated using Equation 1. These waveforms are considered potential hit results. As shown in FIG. 8, the series of waveforms 44 are mapped over the actual collected data 46. One of the waveforms 44 is selected as a best fit hit result by employing known least squares regression techniques. The non-selected waveforms are discarded. The selected best fit hit result, a cosine wave, is governed by the algorithm function above. Therefore, the additional variables of peak linear acceleration a and the hit location b in degrees can be determined by simply viewing the particular mathematical components of the selected best fit result. Thus, the magnitude of the linear acceleration and direction of impact can be calculated using only single-axis accelerometers.

The function above is employed when the HCS is assumed to be circular. Other functions are employed when the HCS is assumed to be other shapes, such as an ellipse. For an ellipse, the cosine wave hit profile is modified by multiplication of the tangent of the ellipse and by division of the tangent of a circle. Using a similar approach, the function for any geometric shape can be employed to generate the hit profile for a particular body part shape.

Further, rotational acceleration is also capable of being estimated from the linear data obtained from the single-axis accelerometers 14 and the estimation of the magnitude of acceleration and direction of impact. Specifically, In the case of impacts that are not directed towards the center of gravity, as shown in FIG. 2, an axial rotational acceleration is assumed to be induced about the z-axis, parallel to the spine through the neck or in the superior-inferior direction and through the center of gravity 18 of the head 12. The normal component of this rotational acceleration will be recorded by the linear accelerometers according to the following function:

$$a_n = r\omega^2 \qquad (2)$$

where r is the distance from the z-axis passing through center of gravity of the head 12 to the accelerometers 14 and w is the angular velocity of the head 12. In this case, the algorithm for fitting the linear acceleration data to the cosine algorithm above works equivalently and accounts for the offset in linear acceleration data due to the normal component of angular acceleration. This offset defines axial rotational acceleration about the z-axis—and is one of the three components that completely describe the rotational acceleration of the skull. Thus, the rotational acceleration appears in the function in formula (1) above as the offset and can be easily determined from the selected best fit curve. The antero-posterior and medial-lateral bending acceleration of the skull are computed together by multiplying the estimated linear acceleration by the distance to the center of rotation of the neck for the given impact direction. This distance can be fixed for all impact directions, selected from a lookup table, or measured empirically. The estimate of the magnitude of the rotational acceleration of the skull is given as the magnitude of the axial, antero-posterior and medial-lateral bending acceleration of the skull.

Therefore, a further novel aspect of the system and method of the present invention is that computation of rotational acceleration is based on the impact location. Such a computation is made even without the assumption of orthogonality of the accelerometers relative to each other and computation of the impact vector using the fitting algorithm described above to collected data all using only single-axis accelerometers orthogonal to the surface of a body part.

The algorithm set forth above in formula (1) has been validated by comparison to theoretical and experimental data. The known inputs were: 1) number of accelerometers; 2) location on the transverse plane of the head of each accelerometer (measured in degrees), and, 3) magnitude (g's) and location (degrees) of the impact in the HCS. To validate the algorithm, a sensitivity analysis of the independent variables was performed. For a given set of these input variables, the correct (ideal) accelerations were calculated. To simulate variability that would be expected in practical applications of system 30, random noise was added to the location of the accelerometers 14 and to the acceleration values. The algorithm used this noisy data set (repeated 10 times for each parametric set of input variables) to predict the magnitude and location of the simulated hit. These values were then compared to the input (ideal) values. Parametric analyses were performed by changing the number of accelerometers 14, the location of each accelerometer 14 location, the standard deviation of the noise in the location of the accelerometers, and the standard deviation of the noise in the peak acceleration values of each accelerometer.

Sensitivity analyses showed that computed values for peak linear head acceleration and hit location were most sensitive to errors in accelerometer location compared to errors in acceleration magnitude. Table 2 below summarizes the effect on both estimated acceleration parameters and on commercial factors including cost and practical implementation.

TABLE 2

| Parameter | Effect on Decreasing Error in Estimated Peak Acceleration Compared to Actual | Effect on Decreasing Error in Estimated Impact Location Compared to Actual | Effect on System Cost | Effect on Practical Implementation of System in Helmets |
|---|---|---|---|---|
| Increased HMAS Measured Accuracy | ++ | ++ | + | + |
| Increased HMAS Location Accuracy | ++++ | ++++ | + | +++ |
| Increased Number of HMAS Units | +++ | +++ | +++ | ++++ |

Figure 9:
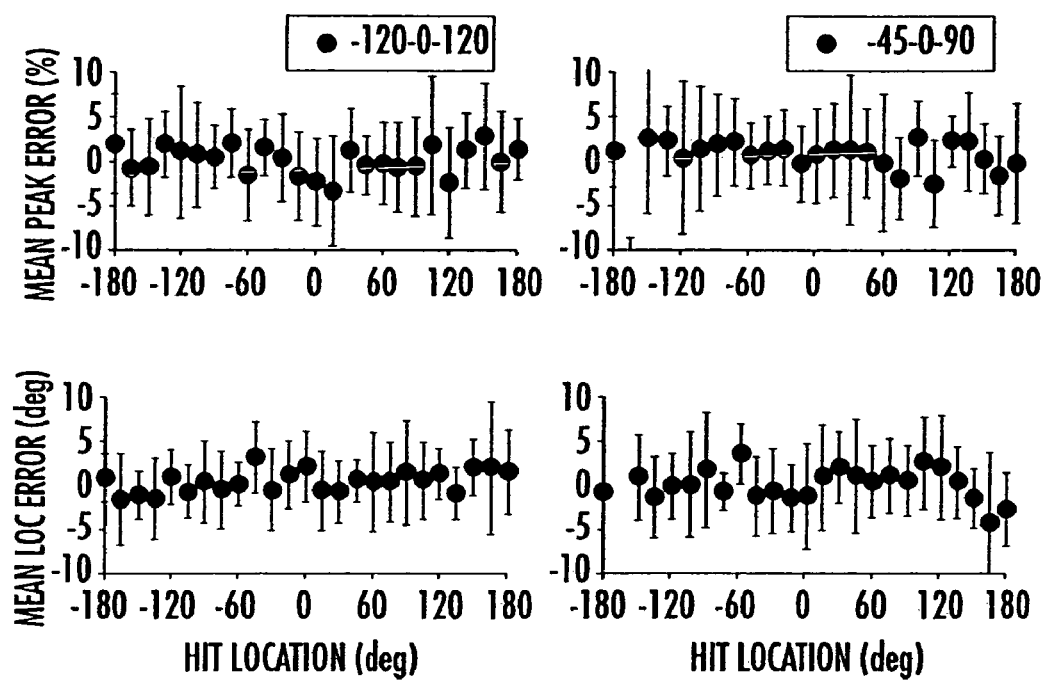
FIG. 9 is a graphical comparison of simulated peak acceleration and location of impact with ideal peak acceleration and location of impact for two sets of accelerometer orientations.

A configuration with 3 accelerometers spaced equally around the coordinate system of FIG. 3 at 120° was sufficient, as shown in FIG. 9, to achieve errors in acceleration magnitude of less than 10%. From a practical perspective, a 3 accelerometer system, with positions at 0°, 120°, −120° (0° was chosen as rear of the head, negative as left side and positive as right side from a rear view of the head as in FIG. 3), demonstrated minimum error in peak acceleration predicted with noisy acceleration data compared to the actual (ideal) input peak acceleration and impact location across all impact locations on the transverse plane. Maximum error was less than 10%. Accuracy did not begin to fall off substantially until the 3 accelerometers were within 30 degrees of one another. There was also only slight decrease in accuracy for asymmetrical accelerometer placements, such as 0°, 90°, −45°, which may be a more practical position for the units to be placed in the helmet. For brevity, the full parametric analysis is not reported.

Increasing from three accelerometers to six accelerometers resulted in a negligible increase in the accuracy of the estimated peak acceleration and estimated impact location for a given accelerometer configuration.

Increasing the number of accelerometers decreased error in estimated peak acceleration and impact location error for 30 g impact simulations (n=10) when the system variables accelerometer acceleration and accelerometer location were perturbed with random noise of 5% and 5 degrees, respectively.

For any single simulation at any hit location, the error did not exceed 10% or 10 degrees. It is concluded that as long as the accelerometer is accurate to within 5% and its location is known within 5 degrees, there is no substantial benefit to increasing the number of accelerometers from three to six. The three accelerometer configuration is preferred from a cost and data management perspective, and meets the desired specifications.

Laboratory testing with a three accelerometer configuration demonstrated that linear accelerations computed from the measured accelerometer accelerations were within 10% for impacts in the transverse plane when compared to an accelerometer at the center of gravity of the headform. Impact location was computed to be within 10° of the actual value. Estimates of rotational accelerations using linear accelerometers were within 10% of computed values using video and direct measurement techniques.

A standard twin-wire drop system (ASTM F1446) was utilized for linear acceleration testing with a triaxial accelerometer mounted at the center of gravity of a standard ISO headform. Peak acceleration from each of the three accelerometers was used as input for estimating the linear acceleration using the least squares fit algorithm described above.

Actual accelerometer locations were measured using a laser protractor system. Five impacts at an impact velocity of approximately 2.2 m/s were recorded at 45° intervals around the transverse plane of the headform. Computed peak acceleration data were compared with linear accelerations measured by a triaxial accelerometer located at the center of gravity of the headform.

A separate guided drop tower (not shown) with free 2D rotation was utilized to compare measured linear and rotational accelerations from both accelerometers and triaxial accelerometer at the center of gravity of the headform with 2D rotational acceleration measured using a magnetohydrodynamic rotational velocity sensor, such as the ARS-01 from Phoenix, Ariz., and computed from a 2D high speed digital video system, such as Redlakes MotionScope (2000 Hz). Accelerations measured by the accelerometers and by the triaxial accelerometer are a combination of linear acceleration and the normal component of the rotational acceleration.

The normal component: $a_n = r\omega^2$, can then be solved for $\omega$. and differentiated to determine the rotational acceleration. Alternatively, the tangential component: at $a_t = r\alpha$, can be solved directly for $\alpha$, the rotational acceleration. We assume that the head and neck acts as a rigid body during the impact. The radius, r, was the distance from the pivot point on the experimental apparatus and the center of gravity of the headform. Error analysis was performed by comparing 2D rotational accelerations estimated from our system with the calculated rotational accelerations from the high-speed video and the ARS sensor. For example, for a 2.2 m/sec drop, rotational accelerations on the order of 2000 rad/sec² were measured from the video, and compared with an estimated 1900 rad/sec² from the linear accelerometers, representing approximately 5% difference.

Thus, the algorithm in accordance with the present invention was validated by demonstrating that the error in estimated peak acceleration and estimated impact location was within ±10% of actual (ideal) when the system variables accelerometer acceleration and accelerometer location were perturbed with random noise of 5% and 5 degrees, respectively. The standard error bars, shown in FIG. 9, illustrate variability with 10 simulations.

Estimates of linear and rotational acceleration from experimental data collected with the system 30 were within ±10% of peak acceleration compared to acceleration measurements taken at the center of gravity of the test headform. Reproducibility of the system was within ±5%.

As shown above, the algorithm for estimating linear and rotational acceleration and magnitude has been validated for 2D and for impacts along the transverse plane. In accordance with the present invention, the algorithm can be readily modified to 3D and tested both theoretically and experimentally.

Therefore, the present invention provides for single axis accelerometers to be incorporated into an helmet such that the accelerometer is in apposition to the surface of the head and can worn by a user. Dual and tri-axis accelerometers may also be used to collect and record additional information, such as acceleration tangent to the surface of the skull, for further analysis and study.

The system 30 of the present invention enables the relationship between biomechanical measures of linear and rotational acceleration and the clinically determined incidence of MTBI across demographic groups to be quantified, with a particular emphasis on children and youth in sports. The system 30 is capable of automatic monitoring of impact incidence and will provide a basis for testing hypotheses relating impact severity and history to MTBI.

Acceleration measurements are highly sensitive to measurement environment and can easily be influenced by local resonance, non-rigid mounting, environmental stochastic noise, etc. Multiple accelerometers may be able to attenuate these effects, but may require an impractical number of sensors and is still influenced by poor acceleration measurements. Further, increasing the number of sensors and using the average of these measurements as the object acceleration is not ideal due to difficulty in mounting and collecting these additional signals and the sensitivity to large measurement errors from accelerometers (averaging is influenced by errors when using a limited number of sensors).

The present invention includes a method to remove measurement noise from a finite number of accelerometers mounted on an object using a pattern recognition approach. A common correlated pattern is created by maximizing the explained variance of this dataset (consisting of accelerometer time histories). Each accelerometer waveform is then recreated using this pattern approach.

Any rectangular matrix (R) can be described by three matrices:

$$USV^T = R$$

where U and V are orthonormal matrices such that $U^R U = 1 = V^T V$ where T is the transpose of a matrix, and the diagonal values in S are the singular values and are ordered so that $S_i > S_{i+1} > 0$.

Taking advantage of the orthonormal properties and applying this to the covariance matrix of the dataset (where columns=times and rows=sensors) allows one to decompose the centered covariance matrix (X) to orthogonal components and sorted by level of importance (i.e, maximizing explained variance or minimizing the sum of square difference):

$$X = \sum_{i=1}^{n} U_i S_i V_i^T$$

The orthonormal basis formed by V describes the underlying time varying patterns between each accelerometer. By orthonormal definition, each pattern described by V is unrelated to the next (orthonormal basis) and ordered by explained variance. For highly correlated data structures (numerous sensors mounted on an object), the first column vector of V will explain close to 100% of all data time variation. It is assumed that all remaining column vectors are associated with noise. Weighted scores for each sensor are determined by multiplying the centered covariance matrix with V. These weights represent the magnitude of V for each sensor. Multiplying the weighted scores (W) with V recreates the entire time history of each accelerometer (a):

$$a_i = \sum_{i=1}^{n} \sum_{j=1}^{m} W_i V_j$$

where n is the number of sensors and m is the number of columns in V. In this manner, measurement noise is eliminated by recreating the sensor waveform using only the first n vectors of V with the associated n weighted scores and setting the remaining weighted scores and vectors to zero and then adding this to the mean waveform from the original dataset.

In addition to utilizing a method of noise cancellation, it is desirable to use a method for minimizing parameter estimate errors. The typical least squares formulation for parameter estimation assumes equal weighting for all measures. These parameter estimates, however, can be biased due to poor independent measurements. Moreover, this bias is highly sensitive to the measurement environment, such as mounting technique and local resonance. This is particularly true for measurements of head acceleration in a helmeted sport such as football, where localized deformation of the helmet shell due to impact can produce large accelerations at that site. These localized accelerations are superimposed on the head acceleration and are not able to be filtered since the frequencies of interest are often at similar frequencies as the helmet response.

Estimates of head translational acceleration are typically based on identifying peak acceleration magnitudes from multiple accelerometers located about the surface of the head. Using a finite number of accelerometers (e.g., n=6) places substantial weight on each accelerometer measurement. If any accelerometer over- or underestimates a peak head acceleration, large errors in impact peak head magnitude and location on the head can be induced. To minimize these potential errors, the present invention includes a weighted least squares approach using multiple accelerometers where each weight is a function of waveform features, and where large accelerometer waveform errors that generally indicate poor head acceleration measurement are given a small weight defined by a non-linear function.

The conventional least squares formulation seeks to minimize the sum of square difference between n independent measures:

$$\min \sum_{i=1}^{n} (\beta_i - \psi_i)^2$$

where $\beta$ is the expected $i^{th}$ measurement and $\Psi$ is the actual measurement from the $i^{th}$ sensor. Equal weighting is placed on each measurement independent of signal quality; poor measurements are given the same weight as valid measurements, inducing errors in the parameter estimates.

In the weighted least squares error correction approach, an additional weight term (w) is added to account for poor measurement error:

$$\min \sum_{i=1}^{n} w_i (\beta_i - \psi_i)^2$$

In this formulation, it is assumed that important information may still be present, and maximization of information is an overall objective. Complete elimination of a potentially erroneous sensor measurement reduces the number of sensor measurements placing greater weights on each measurement. This increase in sensor sensitivity may also have a deleterious effect on parameter estimates.

Measurement weightings are scaled from 0-1 and are determined by a linear or non-linear function. For example, a simple ideal template of an acceleration curve was created from the average of all amplitude normalized acceleration time histories from drops performed in a research laboratory. For each accelerometer time history from every impact (n=6), the sum of square difference between the individual normalized acceleration time history and the ideal impact acceleration was calculated. The peak sum of square error was assigned an amplitude weight of zero and the minimal sum of square difference was assigned a weight of one (1). A second order polynomial was used to fit this data to create a continuous non-linear function describing the distribution, where the shape is dependent on the distribution of the sum of square values. In use, the sum of square difference is calculated for all new individual acceleration data and normalized to the peak sum of square error measured from above. This normalized value is then used as an input to the second order polynomial to estimate the proper weight for use in the least-squares equation. Any feature or combination of features, for example dot product of time series, cross-correlation and Mahalanobis distance can be used to quantify the degree of fit between the ideal and measured time histories.

Current accelerometer based systems that measure head accelerations in humans are limited because of strict requirements of accelerometer location, orientation, and quantity. To measure the accelerations in a head coordinate system, where the head center of gravity is the origin, additional external redundant measures are required to eliminate rotational acceleration terms. Such redundant measures include high-speed video or rotational accelerometers.

The present invention further comprises a direct method for measuring the six degrees of freedom ("6 DOF") acceleration of an object that eliminates the strict orthogonal requirements of accelerometer placement and orientation. The acceleration of any point on an object undergoing acceleration can be described by:

$$\vec{a}_i = \ddot{r} + \alpha \times \vec{r} + \omega \times (\omega \times \vec{r}) + 2\omega \times \dot{r}$$

where r is a vector describing the point location in the head coordinate system, and α and ω are the rotational acceleration and velocity of the object about the object center of gravity, respectively. Under the assumption provided by rigid body dynamics that the point does not move relative to the surface of the object, the coriolis term (2ωxr) can be eliminated (equals zero), with only the translational, tangential, and normal acceleration of the object remaining. Since the measurement of the translational and rotational acceleration is of primary interest, and the accurate measurement of the tangential accelerations is assumed, the influence of the orthogonal acceleration due to rotational velocity, or the centripetal acceleration, is minimized such that it can be ignored and/or eliminated. The influence of the centripetal acceleration can be minimized for at least three reasons: (i) the peak angular velocities are ninety degrees out of phase with the angular acceleration; (ii) the distance between the point and the surface of the object is small; and, (iii) the sensitive axis of the accelerometer is insensitive to centripetal accelerations since the sensitive axis is parallel to the axis of rotation. Using an optimization approach, these nine parameters (i.e. the x, y and z directional components of linear acceleration, rotation acceleration, and rotational velocity) can be resolved, however, increasing the number of parameters increases the calculation time and the level of complexity to find the unique solution.

For a given impact H on a rigid body, the tangential acceleration measured at any point is:

$$\vec{a}_i = \vec{r}_{ai} \cdot \vec{H} + ((\vec{\alpha} \times \vec{r}_i) \cdot \vec{r}_{ai})$$

where $r_{ai}$ is the sensitive axis of an accelerometer, α is the rotational acceleration, and $r_i$ is the location of the point in the head coordinate system. By placing a finite number of accelerometers about the surface of an object with the measurement axis, tangential to the surface, an optimization approach is utilized to determine the best combination of translational (H) and rotational (α) acceleration that minimizes the sum of square error between each accelerometer and the expected tangential acceleration:

$$\min \sum_{i=1}^{n} \left[ \left| (r_{a_i} \cdot \vec{H} + \vec{\alpha} \times \vec{r}_i) \right| - a_i \right]^2$$

where n is a finite number of accelerometers, $r_{ai}$ is the sensitive axis direction of the $i^{th}$ accelerometer, H is the translational impact vector, a is the rotational acceleration vector, $r_i$ is the location of the $i^{th}$ accelerometer in the head coordinate system, and $a_i$ is the measured acceleration at the $i^{th}$ accelerometer.

By properly locating and orienting the requisite number of accelerometers about the surface of an object, the translational and rotational accelerations are directly estimated. A set of proper locations and orientations provides a unique solution for any combination of independent rotational and translational accelerations. This method may incorporate constraints in the optimization to use the highly correlated rotational and translational acceleration relationship to provide more stable solutions. Alternatively, one can measure normal accelerations to measure rotational velocities and differentiate to estimate rotational accelerations. Moreover, rotational velocities can be estimated by integrating the rotational acceleration and assuming an integration constant of zero.

A practical limitation of any electronic device having a battery is power consumption. One way to maximize battery life is to implement an intelligent power management protocol to power down any part of the device that is not currently required for operation. With any power management protocol or system, certain events are typically required to initiate power-up and/or power-down cycles. Conventional on/off switches, like single pole, single throw (SPST) or single pole, double throw (SPDT) varieties, are difficult to implement since a user is physically required to turn the device off, and if forgotten, may fully deplete the power source.

Most electronic devices within sports helmets, including two-way radios and the impact monitoring systems disclosed herein, are designed to operate during the course of play and are generally not necessary when the helmet is removed such as while the player is standing on the sideline. Thus, there is an advantage to linking the power management system, including the power-up and/or power-down cycles of electronic devices, to existing helmet hardware in order to minimize power consumption. For almost all helmeted sports, including football, hockey, lacrosse, a secured chin strap is necessary to keep the helmet properly positioned on the player's head. Conventional chin straps are removably secured to the helmet with a plurality of snaps, where one component of the snap is affixed to the helmet shell and the other mating snap component is affixed to the chin strap. The securing of the chin strap after the helmet is positioned on the player's head and the subsequent un-securing of the chin strap prior to removal of the helmet provide well-defined events for use with the power management system of electronic devices positioned within the helmet.

The present invention provides a power management system for use with helmet-borne electronic devices, wherein the device has a power-up and/or power-down cycle with a power switch driven by connection of existing helmet hardware, for example the snaps associated with the chin straps. The on/off functionality of the connection between the chin strap and the helmet can be used to close an electrical circuit, supply power from the battery, and drive power management features of an electronic device associated with the helmet. Similarly, the disconnection of the snap and the helmet opens the circuit and causes the battery to stop supplying power to the electronic devices. Accordingly, the power management system can be used in conjunction with the OCU 34 and/or the accelerometers 14 of the HMSS 32. In addition, the present invention provides a power management system that includes a sensor assembly operably coupled to the OCU 34, wherein the sensor assembly is configured to detect the presence and/or absence of the wearer's head 12.

Figure 10:
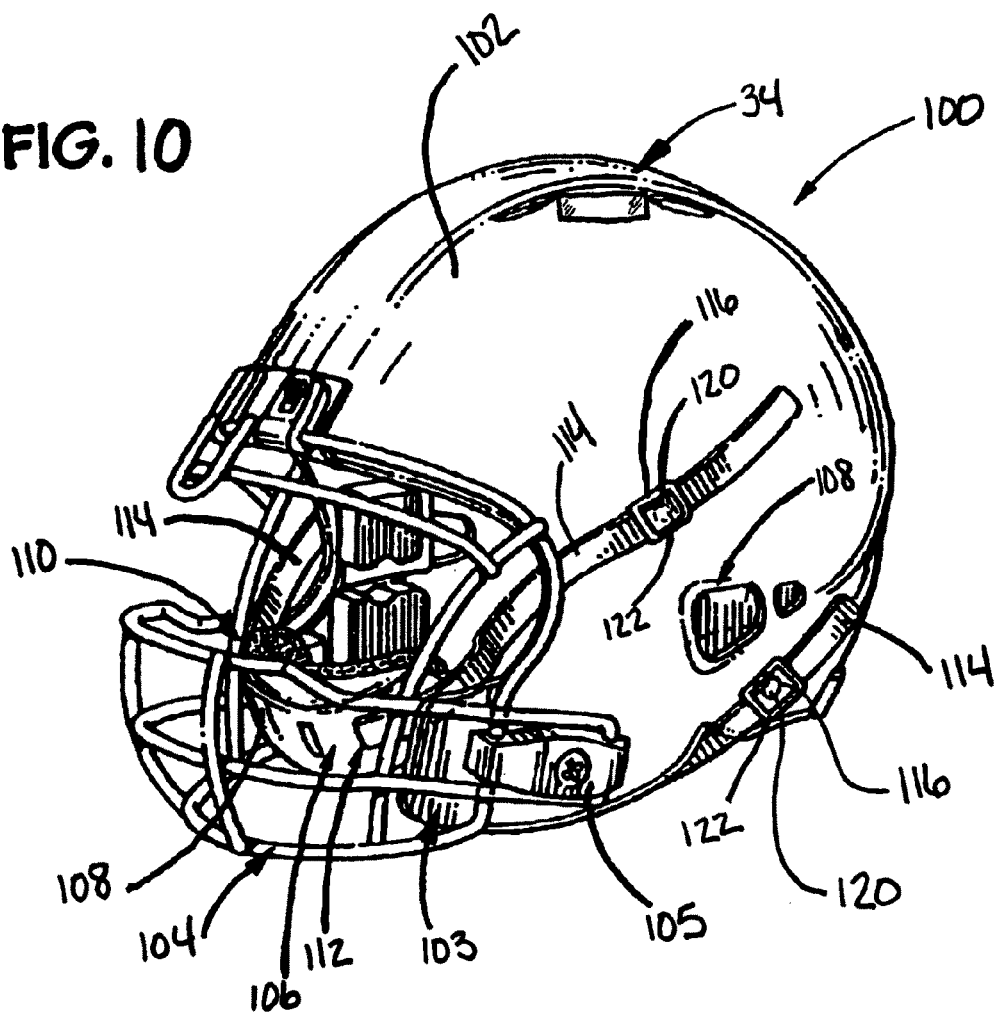
FIG. 10 is a perspective view of a helmet of the invention.
Figure 11:
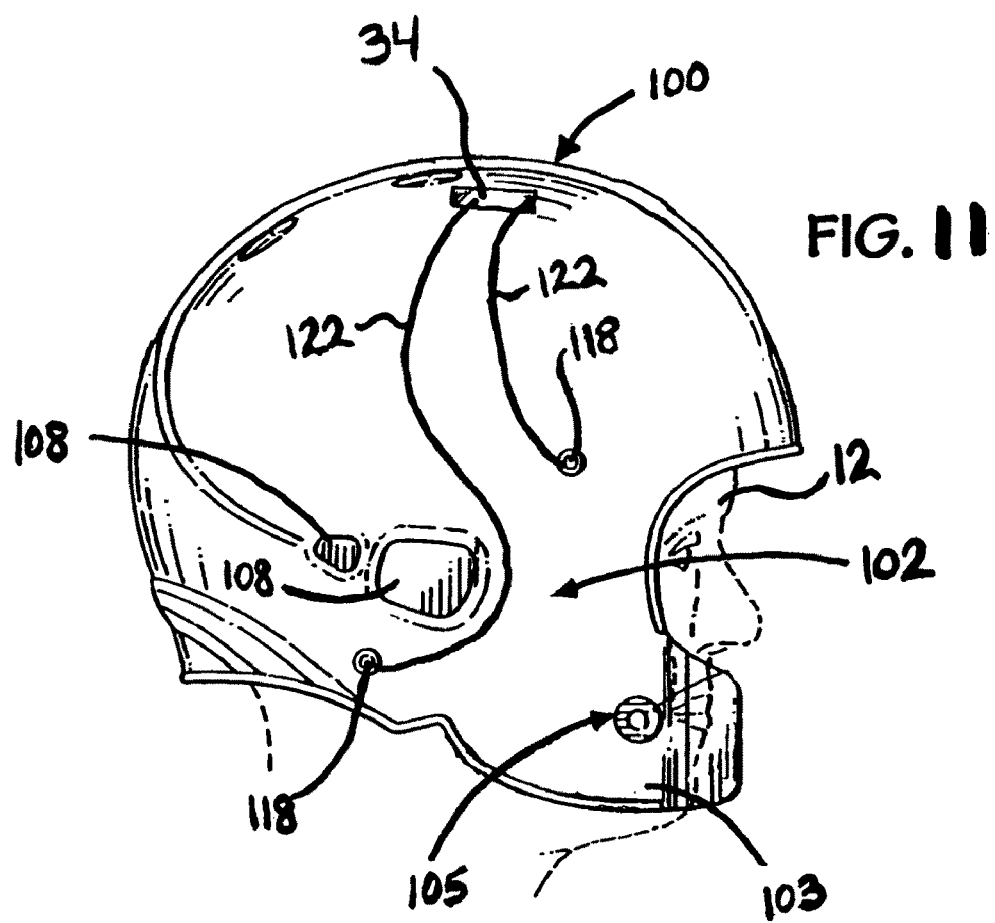
FIG. 11 is a side view of the helmet showing aspects of an electrical circuit.

Referring to FIG. 10, the helmet 100 includes a shell 102 with a forwardly extending jaw flap 103, a face guard 104, a face guard connector 105, a chin strap 106, and ear hole openings 108. The chin strap 106 includes a semi-rigid central portion 109 with internal padding 110 and slots therein 112 that permit insertion of elongated straps 114. The helmet 100 also includes a plurality of snap assemblies 116 to releasably join the elongated straps 114 to the shell 102. The snap assembly 116 includes a male or projecting component 118 (see FIG. 11), and a female or receiving component 120 that is cooperatively dimensioned to receive the projecting component 118 and that is joined to the strap 114 by a slidable buckle 122. Although FIG. 10 shows the electronic device or OCU 34 in the top portion of the shell 102, the device 34 and the acceleration detecting sensors (not shown) can be positioned in other locations of the shell 102. As shown in FIG. 11, the helmet 100 is positioned on a wearer's or player's head 12 and the face guard 104 and the chin strap 106 are removed from the shell 102 to expose the projecting components 118 of the snap assemblies 116.

In one embodiment, the helmet 100 includes a first electrical contact affixed to the shell 102 and a second electrical contact affixed to the strap 114, wherein the contacts can be joined to form an electrical connection that supplies power from the battery to the electronic device. For example, the projecting component 118 of the snap is the first electrical contact and the receiving component 120 is the second electrical contact. Alternatively, a screw used to secure the male component 118 to the shell 102 is the first contact, while the female component 120 on the strap 114 is the second contact. Electrical transmission elements, such as wires or leads extend within the shell 102 from the power supply and the device 34 to the first contact such that when the first and second contact are connected an electrical circuit results. In this configuration, the end of each lead can be nested within the male snap component 118. The first contact can include an electrical insulator, such as a rubber o-ring and nylon insert, for at least one of the leads to prevent conductivity between the leads and maintain electrical separation there between. The second contact can have circular dimensions to facilitate electrical connectivity with the leads of the first contact. Once the two snap components 118, 120 are secured, an electrical connection between the contacts is made. This connection can be used for example, to bring a digital input-output line on a microcontroller located in the helmet 100 to ground, signaling that the switch is on. Further, this switch can be used to control a count down timer to start the power-up and/or power-down sequence. Switch debouncing, the process of reducing bouncing that can occur when the contacts of a switch make contact and rebound an amount before settling to their normal position, can be conducted by the timer, wherein a bounce will simply reset the count down timer.

In another embodiment (not shown), the helmet 100 includes a first contact on one side of the shell 102 and a second contact on the other side of the shell 102. One side of the chin strap 114 includes a third contact that releasably engages the first contact and the other side of the strap 114 includes a fourth contact that releasably engages the second contact. Within the helmet shell 102, a wire extends from one of either the battery or the electronic device to the first contact and another wire extends from the other of the battery or the device to the second contact. Regarding the strap 114, a wire is connected to and extends between the third and fourth contacts. The first and second contacts of the shell 102 can be the male snap components and the third and fourth contacts of the strap 114 are the female snap components. Once the snaps are secured and the strap 114 is connected to the helmet shell, electrical conductivity is made between the first and third contacts and the second and fourth contacts wherein the electrical circuit is closed. The closure of the circuit can be used to initiate a power-up cycle or initiate an interrupt on the micro-controller within the device 34.

In another embodiment, the helmet 100 can include an internal depressable button that is actuated by contact with the head of the player to close the electrical circuit and initiate either the power-up or power-down cycles. With this configuration, the button is depressed when a player puts the helmet 100 on and then released when the player removes the helmet 100. The depression of the button can signal the power-up cycle, while the release of the button can initiate a countdown timer for the power-down cycle.

In yet another embodiment of the power management system, the helmet 100 includes a sensing apparatus or assembly that senses or monitors the presence and/or absence of an object inside the helmet 100 for power management purposes. In general terms, the sensing apparatus is operably connected to the OCU 34 and/or the accelerometers 14 of the HMSS 32. Preferably, the sensing apparatus includes at least one proximity sensor 300 that detects an extent of the wearer's head 12 when the helmet 100 is positioned relatively close to the head 12. Alternatively, the proximity sensor 300 is calibrated to detect a different body part of the wearer, such as the wearer's shoulder region.

The sensing apparatus is calibrated such that the sensor 300 provides a digital on/off relay or digital output signal to activate the power-up cycle before actual physical contact is made between the wearer's head 12 and the internal padding assembly of the helmet 100. Similarly, the sensor initiates the power-down cycle when the helmet 100 is removed from the wearer's head 12 and positioned a specified distance from the wearer's head 12. Further, the proximity sensor 300 can initiate a standby or intermediate status when the helmet 100 is removed, wherein the power management system transitions into either the power-down or power-up cycle after a defined period of time. For example, the power management system goes from the standby status to the power-up cycle when the helmet 100 is placed on the wearer's head 12. In the context of a football or hockey game, the power management system transitions from the off status to the power-up cycle as the player puts on the helmet 100 and enters the field of play from the sideline or locker room. When the player returns to the sideline and removes the helmet 100, the sensor 300 initiates either the power-down cycle or the standby status. When the player re-enters the field of play and puts the helmet 100 back on his head, the sensor 300 initiates the power-up cycle for operation of the HMSS 32 and the OCU 34.

Figure 12:
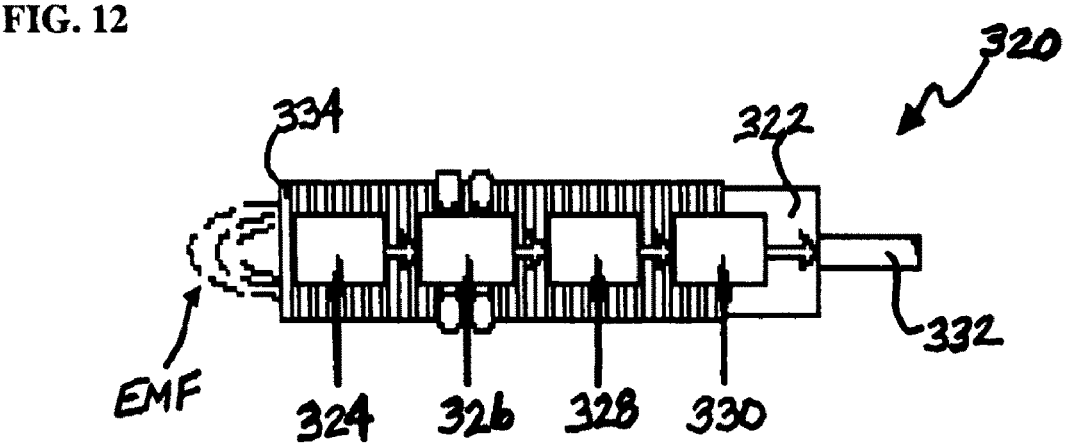
FIG. 12 is a schematic of an inductive proximity sensor of the power management system of the invention.

The proximity sensor 300 can be an inductive sensor 320 that generates an electromagnetic field EMF and detects the eddy current losses generated when the player's head 12 enters the electromagnetic field EMF. Referring to FIG. 12, the inductive sensor 320 generally comprises an elongated housing 322 with a coil on a ferrite core 324, an oscillator 326, a trigger signal circuit 328, an output element or circuit 330, and a wire 332 for connection of the sensor 320 to the OCU 34. As the helmet 100 is engaged and the wearer's head 12 advances into the electromagnetic field EMF, eddy currents are induced causing a loss of energy and a small amplitude of oscillation. The player can wear a removable band or fabric cap (not shown) on his/her head 12 wherein the band or cap has a metallic component to facilitate the disturbance in the EMF. The trigger circuit 328 recognizes a specified change in amplitude and generates a signal that is transmitted through the output 330. The "on" or "off" signal is then transmitted through the wire 332 to the OCU 34 to initiate the power-up or power-down cycle, or the standby status. The outer sensing or active face 334 of the sensor 320 is the surface where the electromagnetic field emerges. Preferably, the sensor 320 is positioned within the shell 102 of the helmet, for example between individual pads of the padding assembly or embedded within a single pad. In this situation, the sensor's active face 334 is oriented towards an interior center point of the helmet 100. Alternatively, the sensor 320 is secured to an outer region of the shell 102 whereby the sensor 320 detects the presence of the wearer's torso or shoulder region for power management purposes.

Figure 13:
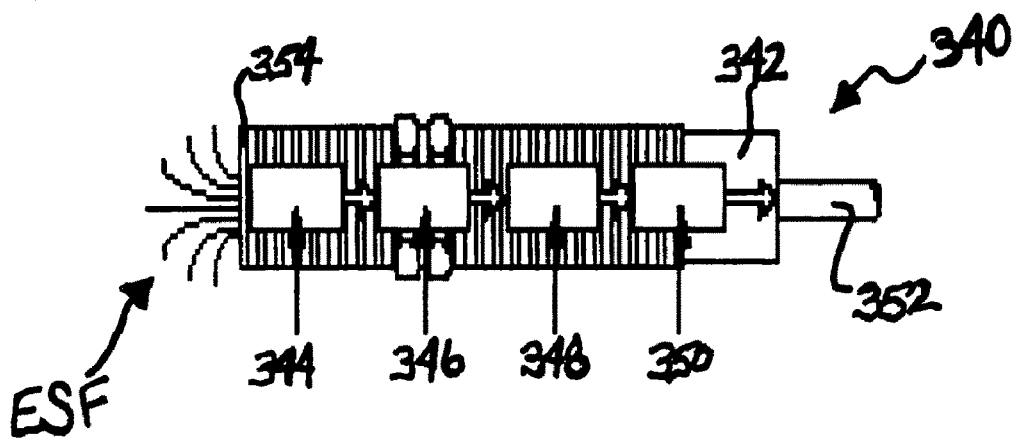
FIG. 13 is a schematic of a capacitive proximity sensor of the power management system of the invention.

The proximity sensor 300 can be a capacitive sensor 340 that operates by generating an electrostatic field ESF and sensing mutual capacitance changes in the field caused when the wearer's head 12 approaches the sensing face 354 of the sensor 340. Referring to FIG. 13, the capacitive sensor 340 generally comprises an elongated housing 342 with a capacitive probe 344, an oscillator 346, a signal rectifier and filter circuit 348, an output circuit 350, and a wire 352 for connection of the sensor 340 to the OCU 34. As the helmet 100 is placed near the wearer's head 12, the head raises the capacitance of the sensor 340. When the capacitance reaches a specified threshold, the oscillator 346 activates and triggers the output circuit 350 to generate an "on" or "off" signal that is used to initiate the power-up or power-down cycle, or the standby status. In general, the capacitance increases as the distance between the wearer' head 12 and the outer face 354 of the sensor 340 is reduced. The capacitance sensor 340 can be shielded or un-shielded, wherein the latter version may include a compensation probe (not shown) that allows the sensor 340 to ignore small amounts of dirt or moisture which may accumulate within the helmet 100 during the course of play.

Figure 14:
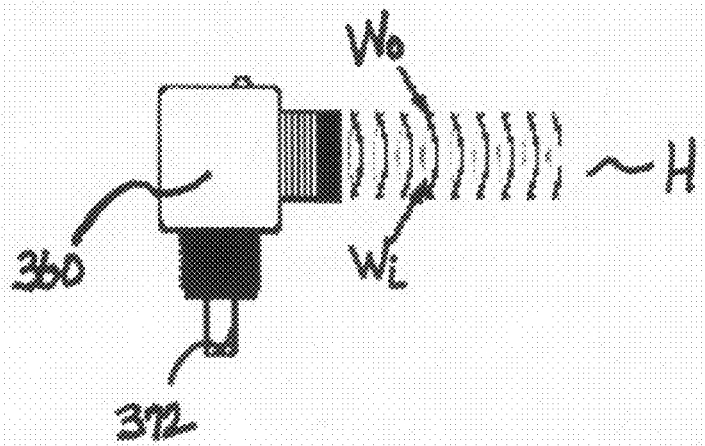
FIG. 14 is a schematic of an ultrasonic proximity sensor of the power management system of the invention; and, FIG. 15 is a schematic of opposed ultrasonic proximity sensors of the power management system of the invention.
Figure 15:
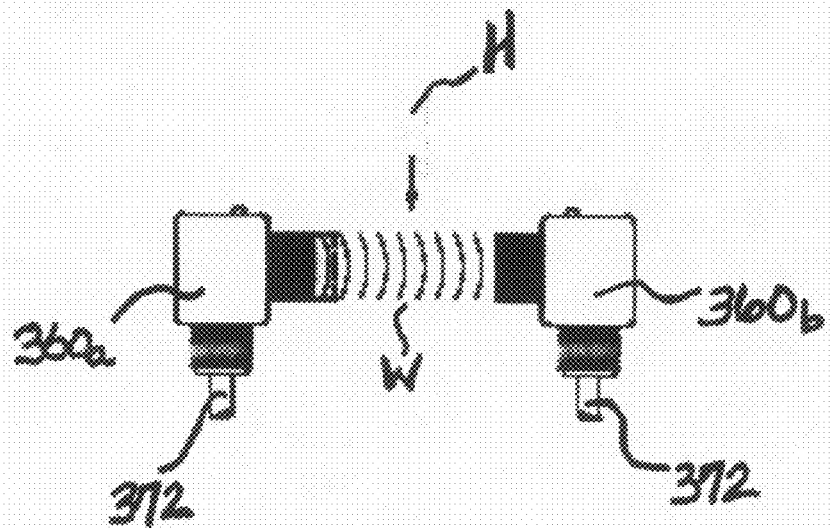

In yet another alternative, the proximity sensor 300 is an ultrasonic sensor 360 that operates by emitting bursts of high-frequency sound waves that reflect or "echo" from the outer surface of the wearer's head 12. The ultrasonic sensor 360 can operate under the diffuse (or echo) mode, or the opposed mode. With the former mode depicted in FIG. 14, a single ultrasonic sensor 360 calculates the distance to the wearer's head 12 by measuring the time required for the sound wave(s) SW to return from the wearer's head 12 and dividing that time value by the speed of sound. Described in a different manner, the sensor 360 emits a series of outbound waves Wo that contact the wearer's head 12 and return to the sensor 360 as inbound wave Wi. With the opposed mode depicted in FIG. 15, a first sensor 360*a* and a second sensor 360*b* are positioned a distance apart within the helmet 100. The first sensor 360*a* emits the sound wave W and a second sensor 360*b*, positioned a distance from the first sensor 360*a*, receives the sound wave W until an extent of the wearer's head 12 interrupts the sound wave W. Both modes allow the sensor 360 to detect objects having a variety of dimensions and formed from material(s) that can sufficiently reflect an ultrasonic pulse. For example, each sensor 360*a, b* is positioned near an ear lobe region of the helmet 100 such that when a leading portion of the wearer's head interrupts the sound wave W, the power management system initiates either the power-up cycle or power down cycle. Each sensor 360 includes a wire 372 for connection of the sensor 360 to the OCU 34.

In addition to the foregoing sensor types, the sensor 300 can utilize other technologies, such as LED, laser, and light (photo-electric) measurement. For example, the sensor 300 can be an infrared LED transmitter/receiver that transmits encoded infrared (IR) waves and then measures the reflection. Since the IR wave is encoded, only the reflected signal with the proper encoding will activate sensor for power management purposes. Further, encoding the IR waves minimizes the false positives caused by the presence of full-spectrum light. Alternatively, the sensor 300 can be an IR sensor that does not encode the wave and is calibrated to sense a finite wavelength, such as body temperature wherein the sensor 300 detects the IR emission of the human body. The sensor 300 can be a light gate which may contain an infrared source and detector aimed at each other to monitor the presence of the player's head 12. The sensor 300 may utilize the Doppler Effect by transmitting narrow wavelength light. As yet another option, the sensor 300 may emit broad spectrum light and measure returned light whereby the sensor monitors what wavelengths have been absorbed by the player's head 12 and what wavelengths have been reflected. The sensor 300 can be a compact limit switch with a plunger-type actuator that makes contact with the player's head 12. Lastly, the sensor 300 can be a magnetic hall effect switch that responds to the presence or the interruption of a magnetic field by producing either a digital or an analog output proportional to the magnetic field strength.

The distance between the active face of the sensor 300 and the wearer's head 12 to send the "on" signal and initiate the power-up cycle of the OCU 34 is often called the operation distance. Conversely, the distance between the active face of the sensor 300 and the wearer's head 12 that causes the "off" signal and initiates the power-down cycle in the OCU 34 is referred to as the release distance. These two distances can be equal or dissimilar, with the release distance being typically greater. In the latter case, the difference between the two distances defines the hysteresis. Hysteresis is often required to prevent sensor chattering, i.e., the rapid switching between on and off signals, that can occur when the proximity sensor 300 (and/or the wearer's head 12) is subjected to shock and vibration. Thus, the proximity sensor 300 in the power management system of the helmet 100 may utilize hysteresis to ensure accurate sensor 300 performance. Furthermore, the proximity sensor 300 can be adjustable such that the operation distance and/or the release distance can be customized by the end-user. For example, the sensor 300 can have a small exterior control knob or an internal circuit that provides for adjustment of the sensitivity.

In one embodiment, the helmet 100 includes a first electrical contact affixed to the shell 102 and a second electrical contact affixed to the strap 114, wherein the contacts can be joined to form an electrical connection that supplies power from the battery to the electronic device. For example, the projecting component 118 of the snap is the first electrical contact and the receiving component 120 is the second electrical contact. Alternatively, a screw used to secure the male component 118 to the shell 102 is the first contact, while the female component 120 on the strap 114 is the second contact. Electrical transmission elements, such as wires or leads 123 extend within the shell 102 from the power supply and the device 34 to the first and second contacts 118 (see FIG. 11) such that when the first and second contacts 118 are connected with the chin strap 106 an electrical circuit results. In this configuration, the end of each lead can be nested within the male snap component 118. The first contact can include an electrical insulator, such as a rubber o-ring and nylon insert, for at least one of the leads to prevent conductivity between the leads and maintain electrical separation there between. The second contact can have circular dimensions to facilitate electrical connectivity with the leads of the first contact. Once the two snap components 118, 120 are secured, an electrical connection between the contacts is made. This connection can be used for example, to bring a digital input-output line on a microcontroller located in the helmet 100 to ground, signaling that the switch is on. Further, this switch can be used to control a count down timer to start the power-up and/or power-down sequence. Switch debouncing, the process of reducing bouncing that can occur when the contacts of a switch make contact and rebound an amount before settling to their normal position, can be conducted by the timer, wherein a bounce will simply reset the count down timer.

The power management system of the present invention provides a number of advantages. First, the helmet 100, including the existing hardware, does not require significant modification for mounting of the switch. Second, the power-up and/or power-down sequence events coincide with actual playing events. In this manner, the power management system extends the life of the battery mounted in the helmet 100. Third, the individual player wearing the helmet 100 does not have to remember to turn the electronic device on or off, which also extends the battery life. Fourth, the proximity sensors 300 enjoy relatively small dimensions thereby permitting installation within the helmet 100 without compromising the fit and comfort of the helmet 100.

As mentioned above, the OCU 34 contains the battery or battery pack, the transmitter, and signal conditioning for the accelerometers. A battery pack that is continually removed and re-inserted into the OCU may increase the likelihood of connector and/or wire failure. Furthermore, a removable battery pack must conform to a form factor that is physically constrained to ease insertion and removal; however, the form factor often limits overall power capacity. Unlike a removable battery, an embedded, rechargeable battery has relaxed physical constraints and can be designed to optimize energy capacity, but charging of this type of battery is more complex. A connector can be used to charge a battery, but repeated insertion and removal of connectors can result in a higher failure rate. To reduce the likely failure of battery connectors from daily removal and insertion for battery charging, the OCU 34 includes a rechargeable battery (e.g. Li-polymer) with slight modifications to the existing helmet hardware to allow it to act as both a mechanical fastener and an electrical charging connector.

The present invention utilizes helmet hardware, for example one or more snap assemblies 16 as electrical conduits for recharging the battery with an external power source. In one embodiment, two male or projecting components 118 affixed to the shell 102 are electrically connected to the OCU 34. Specifically, a pair of leads is connected between either the battery or the electronic device and a first male component 118. A second male component 118 is electrically connected to the battery with a lead for grounding purposes. As part of the battery charging process, a cooperatively dimensioned female connector linked to the external power source is coupled to the first male component 118. During the charging process, current flows from the external power source through the first male component 118 to the rechargeable battery within the OCU 34. A diode may be used at selected locations of the power path to regulate current flow along the path, thereby reducing the likelihood of damage to the components and devices within the OCU 34. Preferably, a diode is positioned between the battery and the device(s) of the OCU 34. An external circuit may be used to monitor the power source to ensure proper charging of the battery.

In a another embodiment, a modified screw of the helmet hardware, such as that used to secure a snap 116 or the face guard 104 to the shell 102, encapsulates a female barrel connector located through the center of the screw. The barrel connector is electrically connected to the battery with wires or leads. An external power source interfaces with the barrel connector using a cooperatively dimensioned male connector with at least one lead that mates with the leads of the barrel connector. Due to the connection between the male and barrel connectors, current can flow from the external power source to the battery for recharging purposes. A diode can be employed along the power path to regulate current flow and reduce the likelihood of damage to the components and devices within the OCU 34. Preferably, a diode is used between the battery and barrel connector to control current flow. A durable cap or cover insertable into the barrel aperture and operably connected to the outer portion of the screw can be utilized to prevent contamination and premature wear when the battery is not being charged. The cap can be fabricated from a variety of materials, including a plastic or elastomer.

While the specific embodiments have been illustrated and described, numerous modifications come to mind without significantly departing from the spirit of the invention, and the scope of protection is only limited by the scope of the accompanying claims.

We claim:

1. A protective sports equipment assembly worn on a user's body part, the sports equipment assembly comprising:
   a padding assembly;
   a battery;
   an electronic device having a processor, a plurality of accelerometers configured to measure an impact to the equipment, and a wireless transmitter to transmit data received from the accelerometers, wherein each accelerometer resides within a bladder housing inserted in the padding assembly, and wherein the accelerometers are positioned adjacent the user's body part; and,
   a sensor that sends a first digital signal to the electronic device to initiate operation when the sensor detects the presence of the body part, and a second digital signal to the electronic device to cease operation when the sensor detects the absence of the body part.

2. The protective sports equipment assembly of claim 1, wherein the sensor generates the first signal when the body part is at a first distance from the sensor, and generates the second signal when the body part is at a second distance from the sensor.

3. The protective sports equipment assembly of claim 1, wherein the sensor includes a photoelectric sensor that detects either the presence or absence of the body part.

4. The protective sports equipment assembly of claim 1, wherein the sensor includes a capacitive sensor that generates an electrostatic field to detect either the presence or absence of the body part.

5. The protective sports equipment assembly of claim 4, wherein the capacitive sensor is unshielded and includes a compensation probe.

6. The protective sports equipment assembly of claim 1, wherein the sensor includes a first ultrasonic sensor that emits high-frequency sound waves to detect either the presence or absence of the body part.

7. A sports helmet comprising:
   a shell;
   a battery powered electronic device positioned within the shell; and,
   a proximity sensor that sends a first signal to the electronic device to do one of either initiate operation when the sensor assembly detects the presence of an object within the helmet, or cease operation when the sensor assembly detects the absence of the object, wherein the sensor is a capacitive sensor that generates an electrostatic field to detect the presence or absence of the object in the helmet.

8. The sports helmet of claim 7, wherein the sensor sends a second signal to the electronic device to do the other of either cease operation when the sensor assembly detects the absence of the object, or initiate operation when the sensor assembly detects the presence of the object.

9. The sports helmet of claim 7, wherein the electronic device includes a plurality of accelerometers that measure acceleration of the helmet wearer's head and a wireless transmitter.

10. The sports helmet of claim 9, wherein shell includes an internal padding assembly having a plurality of pad elements, and wherein each accelerometer is positioned within a pad element.

11. The sports helmet of claim 10, wherein the pad element has a first portion positioned against an inner surface of the shell and a second portion against the wearer's head, and wherein the accelerometer is positioned at the second portion and oriented towards the wearer's head.

12. A sports helmet comprising:
a shell having opposed side portions and a strap to releasably secure the helmet to a wearer's head;
a battery powered electronic device comprising a processor linked with a plurality of sensing devices configured to detect acceleration upon an impact to the helmet, and a transmitter to transmit data received from the sensing device; and,
a switch for the electronic device, wherein the switch includes both a first electrical contact extending outwardly from an outer surface of the shell and a second electrical contact affixed to the strap, wherein when the first and second electrical contacts are joined an electrical connection results.

13. The sports helmet of claim 12, wherein the first electrical contact is a male snap component affixed to the shell.

14. The sports helmet of claim 13, wherein the second electrical contact is a female snap component affixed to the strap.

15. The sports helmet of claim 12, wherein at least one of the first and second electrical contacts has an insulator.

16. The sports helmet of claim 12, wherein the sensing devices are one of single axis accelerometers and multi-axis accelerometers.

17. The sports helmet of claim 12, wherein the electronic device has a power-up cycle that is initiated by the electrical connection between the first and second contacts, and wherein the electronic device has a power-down cycle that is initiated upon the disruption of the electrical connection between the first and second contacts.

18. The sports helmet of claim 12, wherein the first electrical contact is configured to releasably connect with an external power source for recharging of the battery.

19. A sports helmet comprising:
a shell that receives a wearer's head;
a head acceleration measuring unit residing within the shell and including:
a battery;
a microprocessor;
a bladder housing having an accelerometer that measures head acceleration and that is positioned between the shell and the wearer's head; and,
a proximity sensor that sends a first signal to the processor to initiate a power-up cycle when the sensor detects the presence of the wearer's head within the shell, and a second signal to the processor to a power-down cycle when the sensor detects the absence of the wearer's head.

20. The sports helmet of claim 19, wherein the bladder housing includes a pad element positioned between the shell and the accelerometer.

21. The sports helmet of claim 19, wherein the head acceleration measuring unit comprises a plurality of bladder housings.

22. The sports helmet of claim 21, wherein the shell includes a padding assembly, and wherein the bladder housings collectively define a band that is inserted within the padding assembly of the shell.

23. The sports helmet of claim 21, wherein the accelerometers transmit acceleration data to the processor by leads that extend through the bladders and that are connected to the microprocessor.

24. The sports helmet of claim 21, wherein the bladders are formed by a radio frequency welding process.

25. The sports helmet of claim 23, wherein the head acceleration measuring unit includes a wireless transmitter that transmits data from the microprocessor to a remote location.

26. The sports helmet of claim 19, wherein the head acceleration measuring unit also includes a temperature sensor that senses the temperature within the shell.

27. The sports helmet of claim 19, wherein the proximity sensor sends a third signal to the processor to initiate a standby status when the sensor detects the absence of the wearer's head, and wherein the processor initiates a power-up cycle or a power-down cycle from the standby status after a defined period of time.

28. The sports helmet of claim 19, wherein the sensor is a photoelectric sensor that detects either the presence or absence of the wearer's head.

29. The sports helmet of claim 19, wherein the sensor is a capacitive sensor that generates an electrostatic field to detect either the presence or absence of the wearer's head.

30. The sports helmet of claim 19, wherein the sensor is an ultrasonic sensor that emits high-frequency sound waves to detect either the presence or absence of the wearer's head.

31. The sports helmet of claim 19, wherein the sensor is a limit switch that detects the presence or absence of the wearer's head.

32. A sports helmet comprising:
a shell having a first electrical contact and a second electrical contact, each electrical contact extending outward from a side portion of the shell;
a battery powered electronic device including accelerometers that detect acceleration upon an impact to the helmet;
a first lead extending between the electronic device and the first contact;
a second lead extending between the electronic device and the second contact;
a chin strap connectable to the first and second contacts, and wherein the chin strap includes an internal lead; and, wherein the connection of the chin strap to the first and second contacts closes an electrical circuit including the electronic device, the first and second leads and the internal lead of the chin strap.

33. The sports helmet of claim 32, wherein the first contact includes an insulator, wherein the insulator prevents inadvertent electrical conductivity.

34. A sports helmet comprising:
a shell having opposed side portions and a strap to releasably secure the helmet to a wearer's head;
a battery powered electronic device; and,
a switch associated with each side portion of the shell, wherein the switch includes a first electrical contact extending outwardly from an outer surface of the shell wherein the first electrical contact is configured to releasably connect with an external power source for recharging of the battery, the switch further including a second electrical contact affixed to the strap, wherein when the first and second electrical contacts are joined an electrical connection results.

35. A protective sports equipment assembly worn on a user's body part, the sports equipment assembly comprising:
a padding assembly;
a battery powered electronic device including a microprocessor and at least one accelerometer configured to measure an impact to the equipment; and,
a sensor that sends a first digital signal to the electronic device to initiate operation when the sensor detects the presence of the body part, and a second digital signal to the electronic device to cease operation when the sensor detects the absence of the body part.

36. The protective sports equipment assembly of claim 35, wherein the sensor is a capacitance sensor that generates an electrostatic field to detect the presence or absence of the object in the helmet.

37. The protective sports equipment assembly of claim 35, wherein the padding assembly includes a first bladder housing having a pad element and the accelerometer, wherein the accelerometer is positioned adjacent the user's body part.

38. The protective sports equipment assembly of claim 37, wherein the padding assembly further includes a second bladder housing having a pad element and a second accelerometer, wherein the first and second bladder housings define a band that is connected to the padding assembly.

39. The protective sports equipment assembly of claim 38, wherein the accelerometers transmit acceleration data to the processor by leads that extend through the bladder housings and that are connected to the microprocessor.

40. The protective sports equipment assembly of claim 37, wherein the electronic device further comprises a wireless transmitter that transmits data from the microprocessor to a remote location.

41. The protective sports equipment assembly of claim 37, wherein the electronic device further includes a temperature sensor that senses the temperature within the shell.

* * * * *